(12) United States Patent
Ward et al.

(10) Patent No.: US 11,156,219 B2
(45) Date of Patent: Oct. 26, 2021

(54) DISPOSABLE ALTERNATING TANGENTIAL FLOW FILTRATION UNITS

(71) Applicant: Repligen Corporation, Waltham, MA (US)

(72) Inventors: Travis R. Ward, Medford, MA (US);
Steven R. Pearl, Hollis, NH (US);
Adam Malone, Waltham, MA (US);
Tim Erlandson, Hudson, MA (US)

(73) Assignee: Repligen Corporation, Waltham, MA (US)

( * ) Notice: Subject to any disclaimer, the term of this patent is extended or adjusted under 35 U.S.C. 154(b) by 510 days.

(21) Appl. No.: 15/772,761

(22) PCT Filed: Aug. 26, 2016

(86) PCT No.: PCT/US2016/049096
§ 371 (c)(1),
(2) Date: May 1, 2018

(87) PCT Pub. No.: WO2017/082990
PCT Pub. Date: May 18, 2017

(65) Prior Publication Data
US 2018/0238317 A1  Aug. 23, 2018

Related U.S. Application Data

(60) Provisional application No. 62/253,513, filed on Nov. 10, 2015.

(51) Int. Cl.
*F04B 43/073* (2006.01)
*F04B 53/16* (2006.01)
(Continued)

(52) U.S. Cl.
CPC ............ *F04B 43/073* (2013.01); *B01D 61/20* (2013.01); *B01D 61/22* (2013.01);
(Continued)

(58) Field of Classification Search
CPC ........ F04B 43/02; F04B 43/06; F04B 43/073; F04B 45/04; F04B 45/053; F04B 43/0054;
(Continued)

(56) References Cited

U.S. PATENT DOCUMENTS 2,317,073 A    4/1943  Martin
2,563,257 A *  8/1951  Loukonen ............. F16L 55/052
                                                138/30
(Continued)

FOREIGN PATENT DOCUMENTS

CH    0525388 A    10/2009
CN    1057786 A    1/1992
(Continued)

OTHER PUBLICATIONS

Extended European Search Report dated Jun. 26, 2020 for European Patent Application No. 20172773.2.
(Continued)

*Primary Examiner* — Christopher S Bobish
(74) *Attorney, Agent, or Firm* — Kacvinsky Daisak Bluni PLLC

(57) ABSTRACT

Disclosed herein are robust disposable alternating tangential flow (ATF) housing and diaphragm pump units and associated methods of manufacturing, testing, wetting, and using the same.

23 Claims, 16 Drawing Sheets

(51) Int. Cl.
- *F04F 99/00* (2009.01)
- *F04B 43/00* (2006.01)
- *F04B 43/02* (2006.01)
- *F04B 43/06* (2006.01)
- *F04B 45/04* (2006.01)
- *F04B 45/053* (2006.01)
- *B01D 61/20* (2006.01)
- *B01D 61/22* (2006.01)

(52) U.S. Cl.
CPC ...... *F04B 43/0054* (2013.01); *F04B 43/0081* (2013.01); *F04B 43/02* (2013.01); *F04B 43/06* (2013.01); *F04B 45/04* (2013.01); *F04B 45/053* (2013.01); *F04B 53/16* (2013.01); *F04F 99/00* (2013.01); *F15B 2201/3151* (2013.01); *F15B 2201/3155* (2013.01); *F15B 2201/3156* (2013.01)

(58) Field of Classification Search
CPC ......... F04B 53/16; B01D 61/20; B01D 61/22; F15B 2201/3151; F15B 2201/3155; F15B 2201/3156
USPC ...................................... 417/413.1
See application file for complete search history.

(56) References Cited

U.S. PATENT DOCUMENTS

| | | | |
|---|---|---|---|
| 2,697,451 A * | 12/1954 | Knauth | F16L 55/052 138/30 |
| 2,751,084 A | 6/1956 | Wilhelm | |
| 2,851,059 A * | 9/1958 | Lucien | F16L 55/052 138/30 |
| RE26,127 E * | 12/1966 | Wade | F16L 21/06 220/321 |
| 3,442,002 A | 5/1969 | Geary | |
| 3,547,560 A * | 12/1970 | Miller | A47L 15/4427 417/375 |
| 3,825,154 A * | 7/1974 | Jaeger | B67D 1/1243 222/136 |
| 4,092,519 A * | 5/1978 | Eaton-Williams | F22B 1/30 220/320 |
| 4,256,583 A | 3/1981 | Lennartz | |
| 4,267,940 A * | 5/1981 | Wade | B65D 45/345 220/316 |
| 4,290,347 A * | 9/1981 | Basch | F04B 43/02 92/102 |
| 4,334,838 A * | 6/1982 | Fessler | F04B 43/0054 417/395 |
| 4,806,484 A | 2/1989 | Petrossian | |
| 4,844,804 A | 7/1989 | Taylor | |
| 5,074,428 A * | 12/1991 | Wildfeuer | B65D 43/0218 220/322 |
| 5,106,501 A | 4/1992 | Yang et al. | |
| 5,128,037 A * | 7/1992 | Pearl | B01D 61/10 210/321.74 |
| 5,286,646 A | 2/1994 | Kearns | |
| 5,303,599 A * | 4/1994 | Welker | F04B 43/06 73/863.84 |
| 5,411,162 A * | 5/1995 | Koziczkowski | C23C 4/00 220/320 |
| 5,458,468 A | 10/1995 | Ye et al. | |
| 5,563,068 A | 10/1996 | Zhang et al. | |
| 5,712,154 A | 1/1998 | Mullon et al. | |
| 5,811,259 A | 9/1998 | Hall | |
| 6,030,005 A * | 2/2000 | Andersson | F16L 23/04 285/233 |
| 6,051,131 A | 4/2000 | Maxson | |
| 6,139,727 A | 10/2000 | Lockwood | |
| 6,295,918 B1 * | 10/2001 | Simmons | F04B 43/0054 92/98 R |
| 6,544,424 B1 | 4/2003 | Shevitz | |
| 6,555,005 B1 | 4/2003 | Zha | |
| 6,569,329 B1 | 4/2003 | Nohren | |
| 6,755,894 B2 | 6/2004 | Bikson | |
| 7,124,908 B2 * | 10/2006 | Sanders | F17C 1/00 220/581 |
| 7,244,357 B2 * | 7/2007 | Herrington | B01D 61/04 210/321.66 |
| 7,614,338 B2 * | 11/2009 | Uehara | F04B 43/0054 29/888.047 |
| 9,446,354 B2 * | 9/2016 | Shevitz | C12M 29/18 |
| 9,663,753 B2 * | 5/2017 | Gebauer | B01D 61/22 |
| 9,993,751 B2 * | 6/2018 | Shevitz | C12M 29/00 |
| 10,081,788 B2 * | 9/2018 | Shevitz | B01D 61/14 |
| 2002/0162785 A1 | 11/2002 | Futselaar | |
| 2003/0121858 A1 | 7/2003 | Yu | |
| 2003/0222006 A1 | 12/2003 | Cella | |
| 2004/0050771 A1 * | 3/2004 | Gibson | F04B 53/20 210/416.1 |
| 2004/0200768 A1 | 10/2004 | Dannenmaier et al. | |
| 2004/0211726 A1 | 10/2004 | Baig | |
| 2004/0222156 A1 | 11/2004 | Yu | |
| 2009/0159521 A1 | 6/2009 | Luning | |
| 2009/0267344 A1 | 10/2009 | Andrei | |
| 2010/0051545 A1 | 3/2010 | Johnson | |
| 2010/0078395 A1 | 4/2010 | Shevitz | |
| 2010/0219115 A1 | 9/2010 | Davis et al. | |
| 2011/0006878 A1 | 1/2011 | Nyffeler et al. | |
| 2013/0014639 A1 * | 1/2013 | Takeshita | F16J 3/02 92/96 |
| 2015/0050166 A1 | 2/2015 | Tracey et al. | |

FOREIGN PATENT DOCUMENTS

| | | |
|---|---|---|
| CN | 104117226 | 10/2014 |
| CN | 104174077 A | 12/2014 |
| EP | 715875 | 6/1996 |
| EP | 1318303 A2 | 6/2003 |
| JP | 54-123584 | 9/1979 |
| JP | 60-1404 | 1/1985 |
| JP | 01067206 | 3/1989 |
| JP | H05-505540 | 8/1993 |
| JP | 7-47236 | 2/1995 |
| JP | 08-206468 | 8/1996 |
| JP | H11-104412 | 4/1999 |
| JP | 2001-510396 | 7/2001 |
| JP | 2008-82728 | 4/2008 |
| JP | 2010-51910 | 3/2010 |
| WO | WO 2010/036338 | 4/2010 |
| WO | WO 2012/026978 | 3/2012 |
| WO | WO 2013/130176 | 9/2013 |

OTHER PUBLICATIONS

International Search Report and Written Opinion in International Application No. PCT/US2016/49096, dated Feb. 21, 2017, 19 pages.

\* cited by examiner

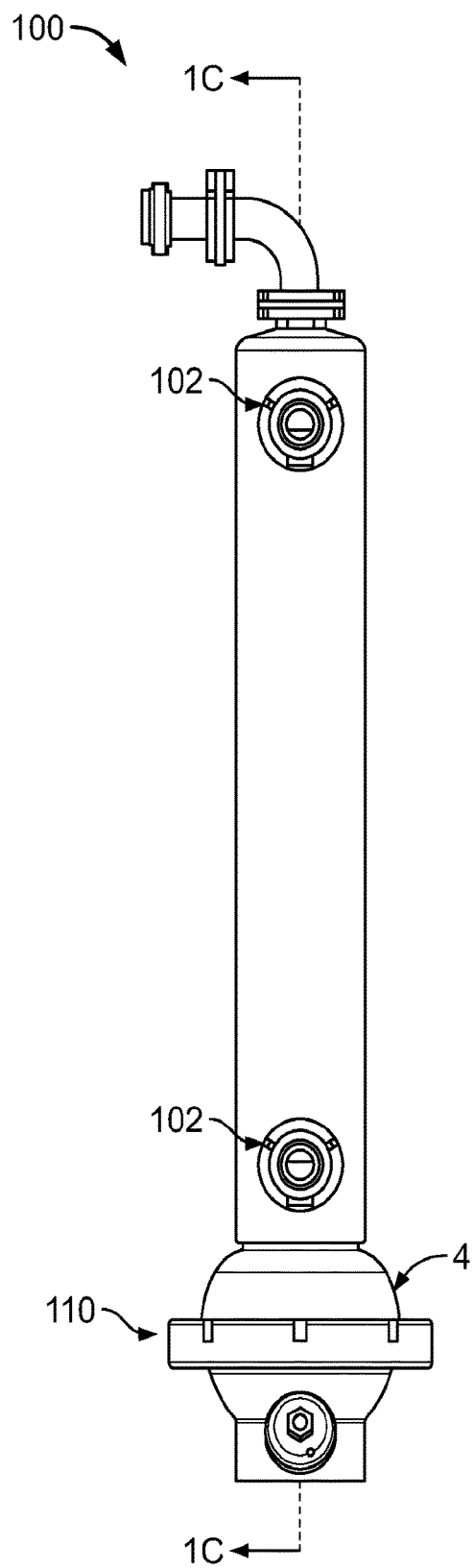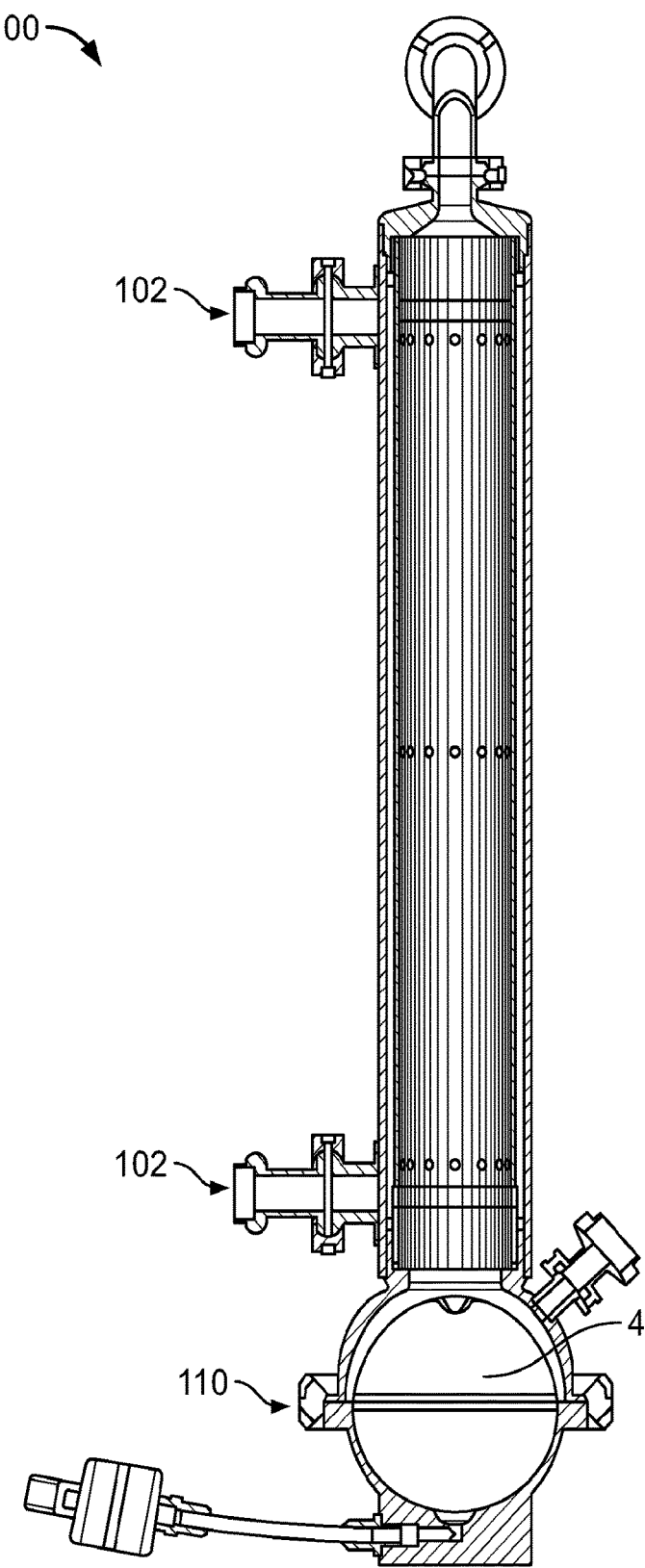
FIG. 1B
FIG. 1C

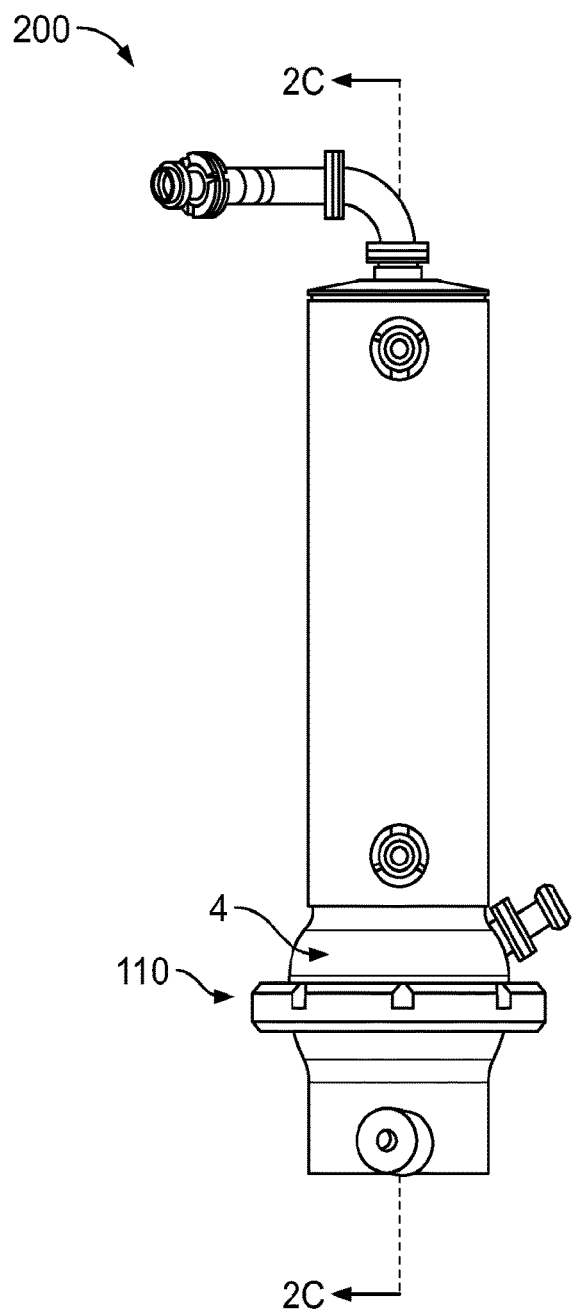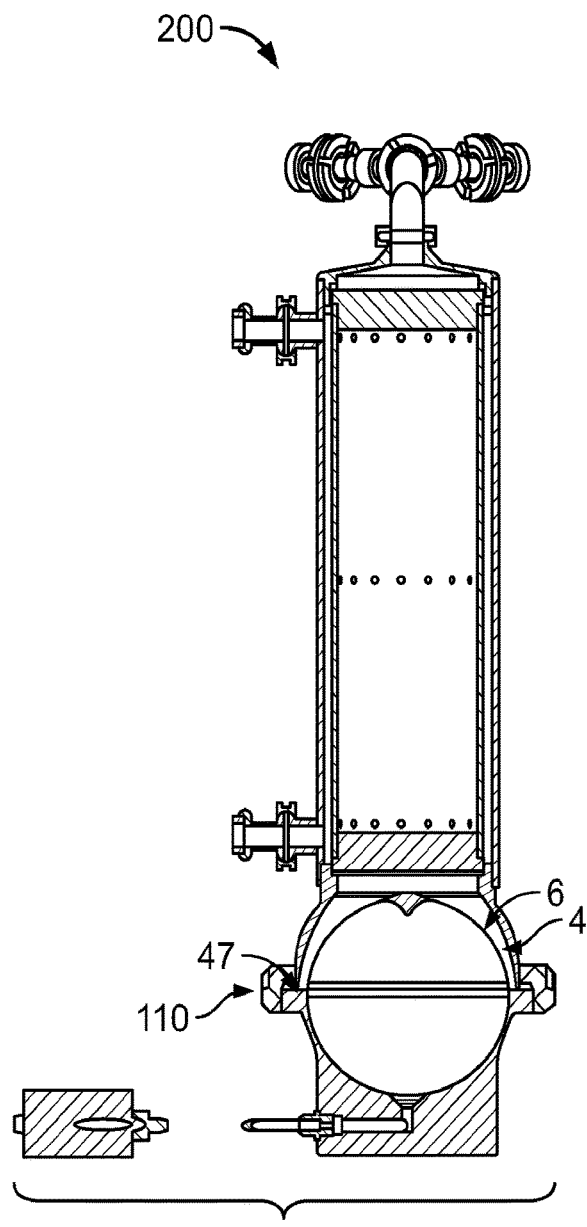
FIG. 2B
FIG. 2C

DISPOSABLE ALTERNATING TANGENTIAL FLOW FILTRATION UNITS

CROSS REFERENCE TO RELATED APPLICATIONS

The present application is the U. S. national stage entry under 35 USC § 371 of International Patent Application No. PCT/US2016/049096, filed on Aug. 26, 2016, which claims priority to U.S. Patent Application No. 62/253,513, filed on Nov. 10, 2015, the entire contents of each of which are incorporated herein by reference.

TECHNICAL FIELD

This invention relates to disposable, alternating tangential flow filtration units that include a housing and a diaphragm pump, e.g., for use in filtration systems, as well as attachments for wetting/flushing the filter while maintaining a sterile environment.

BACKGROUND

Filtration is typically performed to separate, clarify, modify, and/or concentrate a fluid solution, mixture, or suspension. In the biotechnology, pharmaceutical, and medical industries, filtration is vital for the successful production, processing, and analysis of drugs, diagnostics, and chemicals as well as many other products. As examples, filtration may be used to sterilize fluids and to clarify a complex suspension into a filtered "clear" fraction and an unfiltered fraction. Similarly, constituents in a suspension may be concentrated by removing or "filtering out" the suspending medium. Further, with appropriate selection of filter material, filter pore size and/or other filter variables, many other specialized filter uses have been developed; these may involve selective isolation of constituents from various sources, including cultures of microorganisms, blood, as well as other fluids that may be solutions, mixtures, or suspensions.

Biologics manufacturing processes have advanced through substantial process intensification. Both eukaryotic and microbial cell culture to produce recombinant proteins, virus-like particles (VLP), gene therapy particles, and vaccines now include cell growth techniques that can achieve 100e6 cells/ml or higher. This is achieved using cell retention devices that remove metabolic waste products and refresh the culture with additional nutrients. One of the most common means of cell retention is to perfuse a bioreactor culture using hollow fiber filtration using alternating tangential flow (ATF). Both commercial and development scale processes use a device that controls a diaphragm pump to perform ATF through a hollow fiber filter (see, e.g., U.S. Pat. No. 6,544,424) in which the pump and filter are encased in stainless steel and autoclaved prior to use in order to maintain sterility. For economy and flexibility many production facilities are striving to use disposable products, however the conversion of the stainless steel ATF to a disposable pre-sterilized device has substantial challenges.

Large scale production with ATF devices requires a pump chamber housing that can withstand significant force and maintain the integrity of the silicon diaphragm. A means of sealing the diaphragm within the hemispheres of the plastic disposable pump is required. Also, after sterilization of the device with gamma radiation or ethylene oxide the dry filter must be flushed with liquid and the fibers of the membrane wetted in order to obtain efficient perfusion so a device must be designed to allow for a wetting procedure prior to use. Current practices with filtration devices include performing an integrity test to assure that the device is perfusing a liquid solution with the expected rate of fluid flux across the membrane and no leaks in the fibers or device are present that would cause a production failure.

This disclosure describes a disposable ATF device and methods of use that overcome these barriers to constructing and using a disposable ATF device suitable for intensified cell culture production.

SUMMARY

The present disclosure provides a disposable ATF device suitable for supporting high density cell culture processes. This disclosure also provides methods for obtaining a high filtration performance in a sterile environment with the disposable ATF device. The present disclosure is based, at least in part, on the discovery that if you use a sterilizable (e.g., using an autoclave, steam, gamma radiation, ethylene oxide) plastic clamp ring with an internal threading that is specifically designed to function in coordination with top and bottom hemispherical ATF pump chamber halves that have top and bottom flanges, wherein one of the flanges is threaded to mate with the clamp ring, and one or more of the flanges can have additional features to aid in sealing the diaphragm, along with a specially designed interior pump diaphragm, you can simply manufacture a sterile, robust disposable ATF filtration housing and pump unit that can withstand the significant pressures and wide pressure variations inherent in the use of such disposable ATF units in commercial filtration systems.

The present disclosure is also based in part on the configuration of ports and fluid bags that can provide a sterile flush of liquid over the enclosed filter while maintaining sterility in order to prepare the device for alternating tangential flow of the media from a bioreactor without introducing the flush solution into the bioreactor. The ability to use the alternating tangential flow of the ATF device from the diaphragm pump provide a novel mechanism to condition the filter for optimal performance in perfusion processes while maintaining a sterile environment. Methods are described for using serum free growth media to accomplish the flushing and wetting of the filter. This configuration of the ATF device also allows for testing the integrity of the filtration device thus assuring a flux rate performance during operation of the device with the bioreactor.

Development of a functional and robust disposable, rather than metallic, ATF housing and pump unit was difficult due to the significant forces involved in typical commercial uses of these units. Pressure inside the ATF pump varies widely and can rise up to 50 psi or more, which traditionally requires metal (e.g., non-disposable) components that can withstand the resulting forces. To develop a disposable ATF pump, many materials and plastics were tried unsuccessfully. The use of a non-metallic material is complicated by the fact that many adhesives, which could be used to increase adhesion and strength in many applications, are toxic to cells within the pump and so cannot be employed in the present new pumps.

In one aspect, the disclosure provides disposable ATF housing and diaphragm pump units that include a hollow tube of a sterilizable, non-toxic, rigid plastic; a first pump hemisphere secured to an end of the hollow tube, wherein the first pump hemisphere comprises a first circumferential flange; and wherein an opening in the first pump hemisphere enables fluid to flow between the first pump hemisphere and the hollow tube; a second pump hemisphere comprising a second circumferential flange configured to mate with the first circumferential flange, wherein either the first circumferential flange or the second circumferential flange comprises an external threading; a flexible diaphragm configured to be disposed between the first and second circumferential flanges; and a clamp ring having an internal surface comprising an internal threading, wherein the clamp ring is configured to be placed over the pump hemisphere without a threaded circumferential flange and to be secured to the threaded circumferential flange.

In various embodiments, the clamp ring can comprise one or more of acrylonitrile-butadiene-styrene, polyethylene, polyethylene, polycarbonate and polysulfone plastic. In some embodiments, the clamp ring can include a lower portion that has the internal threads and an upper portion that has an internal surface configured to accommodate a curved or angled outer surface of the first pump hemisphere.

In some embodiments, the disposable ATF units can further include one or more ports used to attach any one or more of an air reservoir, a permeate flush bag, and a fluid supply bag through sterile connections to achieve a closed system capable of being operated as an ATF and wet the filter membrane. In general, the ATF units can be pressurized up to 45 psi or higher, e.g., 10, 15, 20, 25, 30, 35, 40, 45, 50, 55, or 60 psi.

In certain embodiments, the first and second flanges have a groove configured to mate with a protrusion on the flexible diaphragm. In general, the clamp ring is configured to compress the flexible diaphragm between the first and second flanges and a level of compression can be changed by applying a torque specification that correlates to sufficient compression of the diaphragm to contain pressure at several orders of safety in the design. For example, the torque specification can be approximately 10 to over 100 lbft, e.g., approximately 10 to 100 lbft, 20 to 80 lbft, or 30 to 70 lbft, e.g., 10, 20, 30, 40, 50, 60, 70, 80, 90, or 100 lbft.

In another aspect, the disclosure provides methods of preparing a fully wetted disposable filtration device. The methods include connecting retentate and permeate fluid bags to top ports of a disposable alternating tangential flow (ATF) unit as described herein using sterile connections; attaching a media or other fluid containing bag to a pump inlet port; and operating the disposable ATF unit to achieve flux of media or other fluid across a filter membrane within the hollow tube of the disposable ATF unit. These methods can further include draining retentate fluid from the disposable ATF unit through the pump inlet port after operating the disposable ATF unit to achieve fluid flux to permeate a chamber within the hollow tube of the disposable ATF unit.

In another aspect, this disclosure includes methods of performing an integrity test of a disposable filtration device. These methods include draining media used to flush a disposable filtration device into a wetting fluid bag with an air pressure source open to raise a diaphragm inside the filtration device; closing an air pressure source valve to release any pressure on the diaphragm; closing a valve located between the wetting fluid bag and a port on the filtration device and a valve connected to a retentate port of the filtration device; pressurizing one side of a filter using the air pressure source; closing a valve between the filter and the air pressure source; measuring the pressure decay versus time; and correlating the measured pressure decay to air flow.

In these methods, the media can be drained by gravity or by pumping the media from the device. In certain embodiments, the air pressure source provides air at a pressure of about 1-5 psi, e.g., 1, 2, 3, 4, or 5 psi.

In another aspect, the disclosure provides methods of performing an integrity test of a disposable filtration device. These methods include draining media used to flush a disposable filtration device into a wetting fluid bag with an air pressure source open to raise a diaphragm inside the filtration device; closing an air pressure source valve to release any pressure on the diaphragm; closing a valve located between the wetting fluid bag and a port on the filtration device and a valve connected to a retentate port of the filtration device; pressurizing one side of a filter using the air pressure source; measuring pressure inside the device versus time; measuring flow between the air pressure source and the device using a flow meter; and correlating the measured pressure to the measured air flow.

In another aspect, the disclosure provides methods of using a disposable filtration device. These methods include obtaining a disposable ATF unit of any aspect of this disclosure, disposing the ATF unit into a fluid circuit by connecting fluid bags to top ports of the ATF unit using sterile connections, and attaching a fluid container to a pump inlet port such that the ATF unit can achieve flux of media or other fluid to be filtered across a filter membrane within the hollow tube of the disposable ATF unit and when the filtration is complete, disposing of the ATF unit As used herein, the terms "sealed," "sealing," and the like refer to the fact that a juncture or junction of two chambers or other systems components does not permit fluid to leak through the juncture or junction at pressures up to 50 psi.

"Flushing" refers to the use of a solution over and through a hollow fiber filter.

"Wetting" refers to the flushing of a hollow fiber filter in a manner in which the fiber membrane pores now contain liquid (wetted) and show low air passage at low pressure and high fluid flux rates.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 1A-1C are isometric, front, and cross-sectional views of a first embodiment of a disposable ATF housing and pump unit as described herein.

FIGS. 2A-2C are isometric, front, and cross-sectional views of a second embodiment of a disposable ATF housing and pump unit as described herein.

Like reference symbols in the various drawings indicate like elements.

DETAILED DESCRIPTION

Figure 1A:
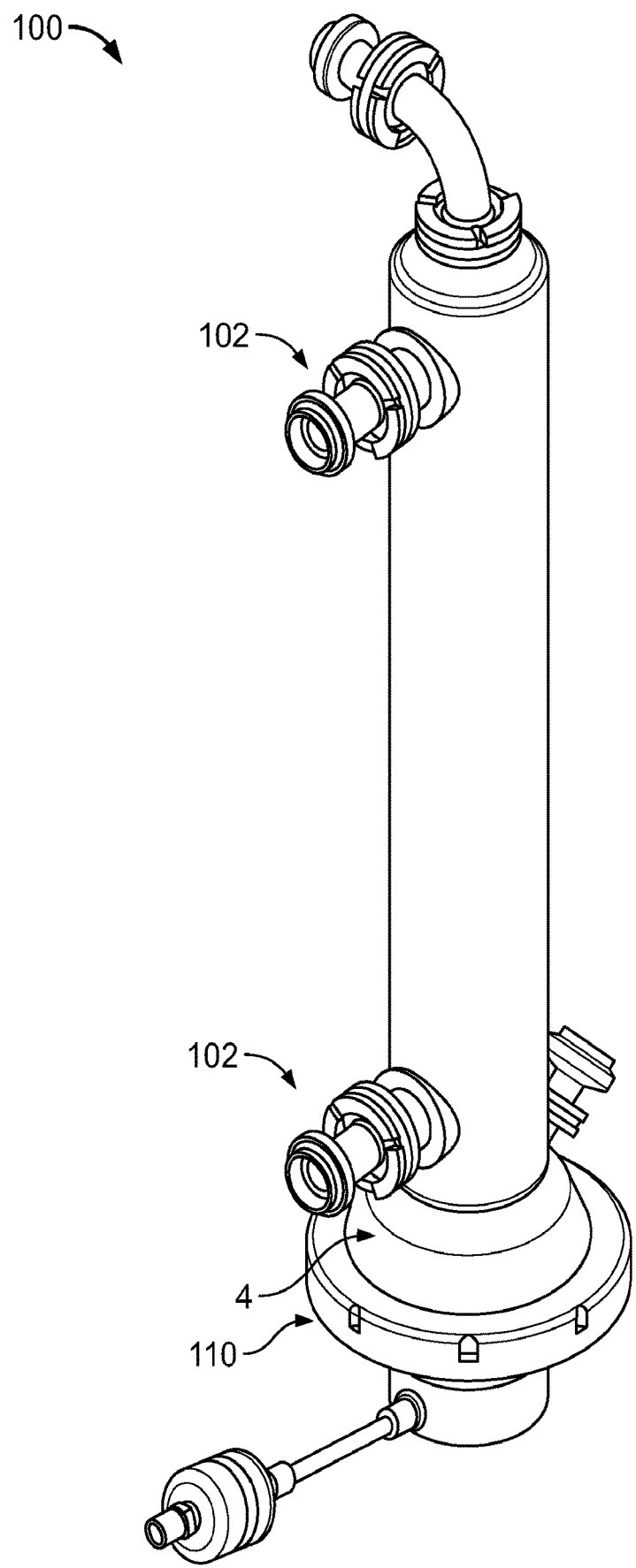

The present disclosure describes new disposable ATF housings and pump units that are sterilizable by common practices (e.g., gamma radiation and ethylene oxide) and are designed to be disposable and/or for single or limited use. The units include a plastic housing connected directly to a spherical ATF pump assembly that includes two hemispherical halves. Given the specific construction, the new units can surprisingly withstand the rigors and significant pressures that arise during use. One hemisphere has an externally threaded flange, and a clamp or lock ring concentrically surrounds one hemisphere and threads onto the opposing hemisphere, squeezing/sealing across an internal pump diaphragm, made of, e.g., silicone or other elastomer. In this embodiment, the clamp ring is internally threaded. A clamp or lock ring could also consist of two units that thread together from the bottom and top across the hemispheres.

These new units are sterilizable, robust, yet disposable, and can be used in place of any ATF filtration systems that currently uses metal housing and pump units. In spite of their disposable nature, the new disposable ATF housing and pump units can withstand cycling of significant pressures that are inherent in the commercial use of such ATF systems. The disposable ATF design includes fluid path configurations that allow flushing and wetting the filter while maintaining sterility. The configurations also allow for filter integrity testing of the ATF device that will ensure the proper performance of the filtration device.

With advancements in new materials and manufacturing methods in recent years, the construction and use of disposable equipment has gained increasing acceptance. Such disposable systems can be set up with minimal handling and do not require cleaning or sterilization by the user. They are supplied sterile and in a form ready to use with minimal preparation and assembly. This results in cost savings due to reduced labor and handling by the user along with elimination of a long autoclave cycle. Furthermore, at the end of their use, the systems can be readily discarded without disassembly or cleaning. These systems reduce risk of contamination and assembly by operators. They do not require lengthy validation procedures for operation/sterilization. These units are lighter and easier to transport, and are less expensive and take up less storage space compared to stainless steel or glass units. Also this eliminates autoclaving which is cumbersome and problematic. Another option to sterilize equipment is to Steam In Place (SIP); this product would remove the need for a large steam generator and piping. The new systems also reduce the amount of liquid waste fluids since they will remove the need for washing parts and parts washing validations. The convenience of these systems will drastically reduce the implementation time at the manufacturer's site.

However, significant pressure cycling resulting in pressure gradients and flows that are both axial and radial to the fiber membrane surface are inherent in the ATF process, and exert substantial internal forces on all ATF filtration and pumping systems. During the "pressure cycle," the pressure in the pump is greater than the pressure in the retentate reservoir and can rise as high as 25 psi or more. The liquid flows "forward" from the diaphragm pump in an axial direction, i.e., through the filter element towards the retentate reservoir. Also, some of the liquid is forced through the filter membrane into the filtrate compartment. Therefore, with an enclosed filtrate compartment, the influx of filtrate can pressurize the filtrate compartment to significant levels during cycling due to the restrictions at the permeate outlet (pump).

These cyclic pressures make it difficult to create a robust, commercially useful ATF filtration system that is also sterilizable and made of materials that are disposable. Building, assembling, and adhering these materials in a simple, easy, robust, cost effective, and manufacturing friendly manner is challenging and the choices of materials that can be used as described herein are limited due to the high pressures, extractables/leachables profiles, the medical grade certifications required, transparency, cost, sterilizability, and availability. Forces in the hemisphere assembly are magnified due to the geometry and the large surface area. As a result, sealing of the pump (air/liquid sides) and the filtration module feed to permeate and external environment are difficult design challenges. Another challenge that was overcome in this design was creating an assembly that would enclose and seal around various sized filter cartridges from different vendors.

Disposable ATF Housing and Pump

FIGS. 1A-C, 2A-C, and 3A-C show isometric, front, and cross-sectional views of three different embodiments of disposable ATF housing and pump units 100, 200, and 300, respectively, as described herein.

In general, the housing, the diaphragm pump, the internal diaphragm, valves, filters, and other constituents of the new ATF housing and pump units can be constructed from materials that meet certain requirements. In particular, the materials must withstand the pressures generated during operation of typical fluid filtration systems, be free of toxins that can harm or kill cells or microorganisms, be readily molded into desired shapes, be light and relatively inexpensive, and must be able to be ethylene oxide (EO) or gamma radiation. For example, useful materials include polycarbonate (PC) (e.g., HPS grade from Sabic), polysulfone (PS), copolyesters of BPA-free plastics (e.g., TRITAN® from Eastman Chemical Co.), polypropylene (PP), nylon, glass-filled polymers, ultra-high-molecular-weight polyethylene (UHMWPE), polyether ether ketone (PEEK), and composites (e.g., glass/PC, glass/PS, and glass/nylon). Additional desired features of these materials include their suitability for various manufacturing techniques described herein, amenability to packaging and storage, transportability, biocompatibility, and their protection against damage or contamination of the contents processed therein.

Figure 6A:
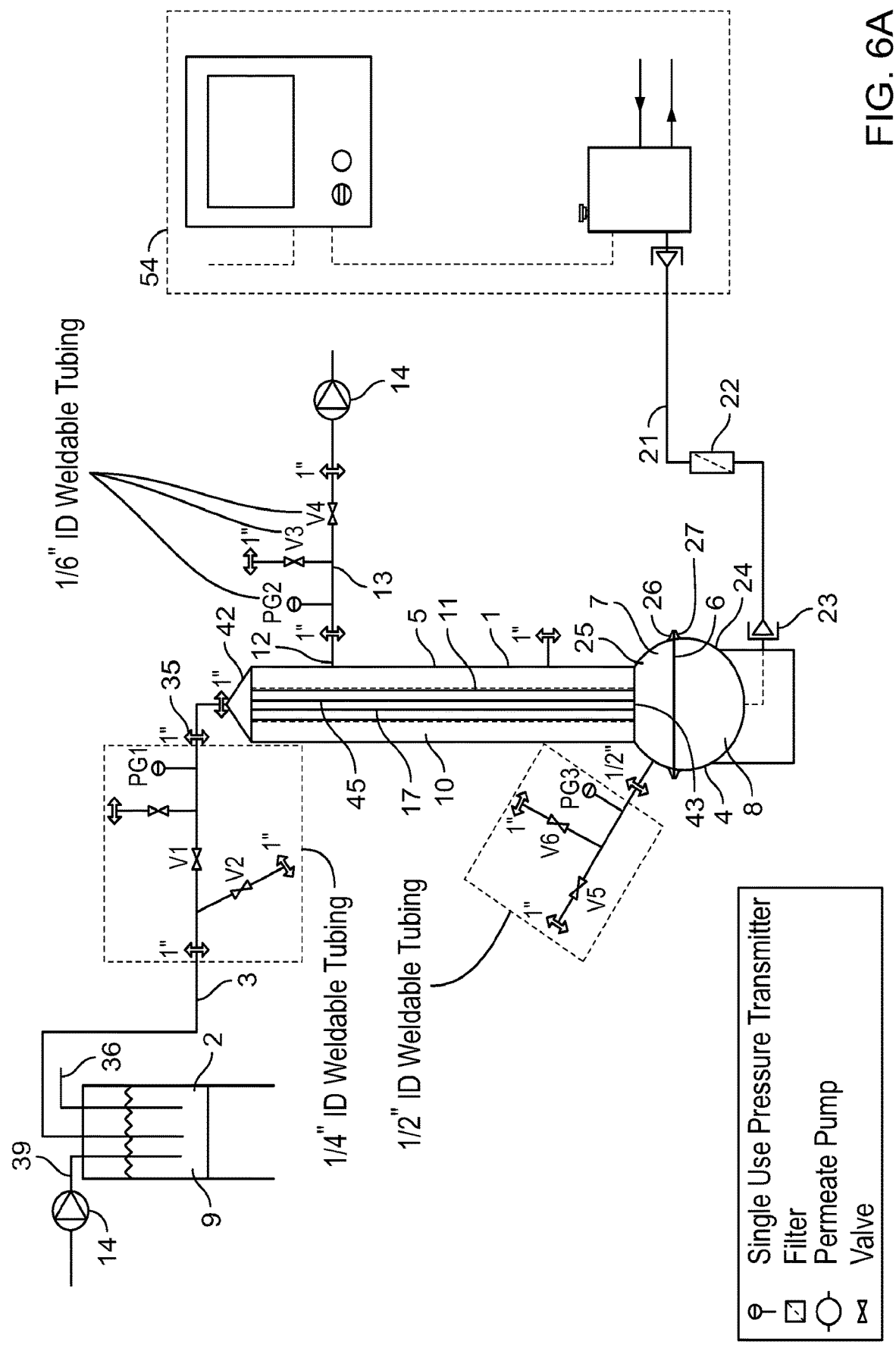
FIG. 6A is a system level representation of a disposable ATF pump housing connected to a controller and a bioreactor.

FIGS. 1A-1C are views of an embodiment of a disposable ATF housing and pump unit 100 that includes a disposable clamp ring 110 and can be used in the ATF filtration system illustrated in FIG. 1C (described in further detail below). In this embodiment, permeate ports 102 are included at upper and lower ends of the filter housing 5 (as shown in FIG. 6A) in addition to the entrance end 42 of filter housing 5 and air inlet port 23 shown in FIG. 6A. The clamp ring can be made of a rigid, machinable or moldable plastic, as described herein, e.g., acrylonitrile butadiene styrene (ABS), polyethylene (PE), PP, PC, PS, nylon, a glass-filled polymer, or a composite.

Figure 2A:
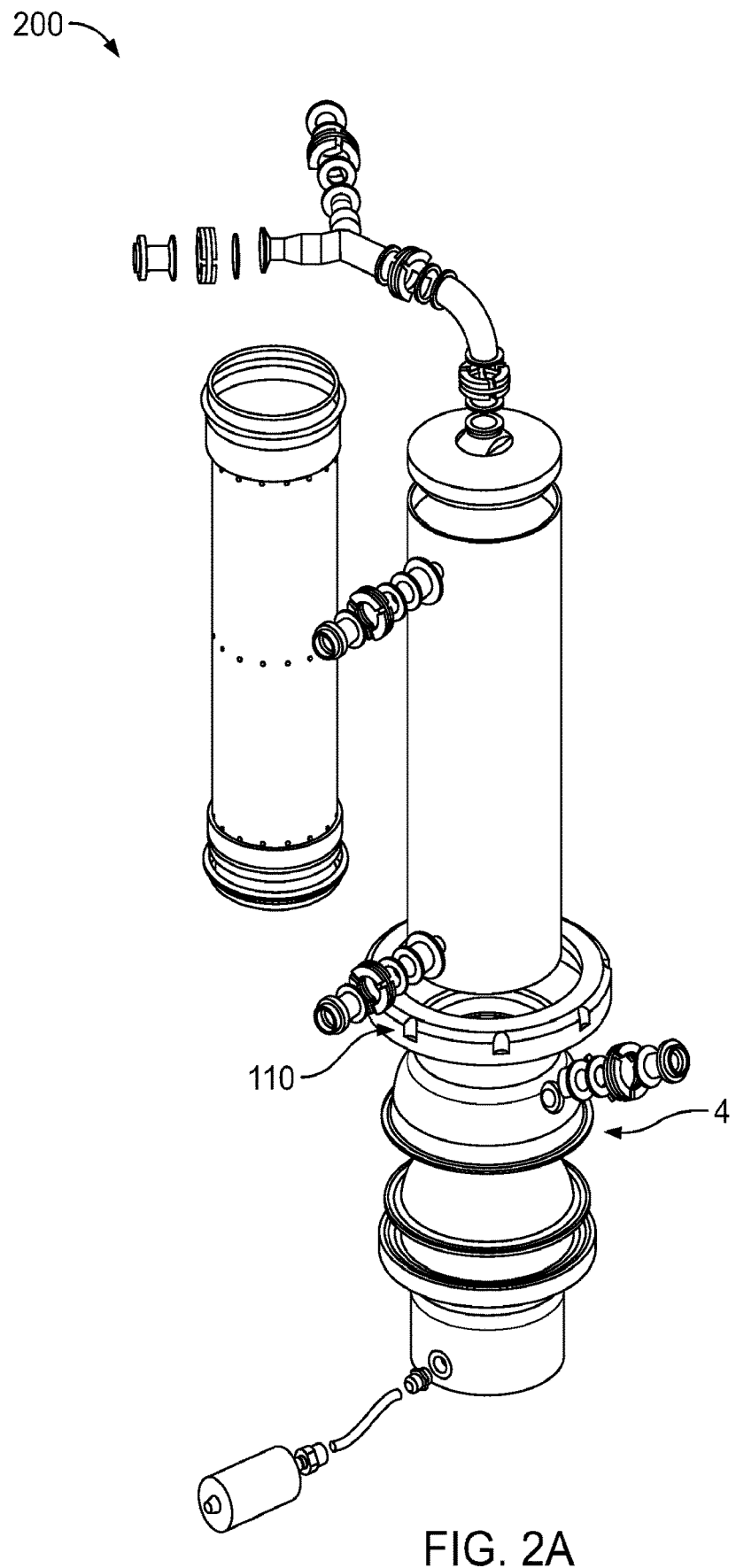
Figure 3A:
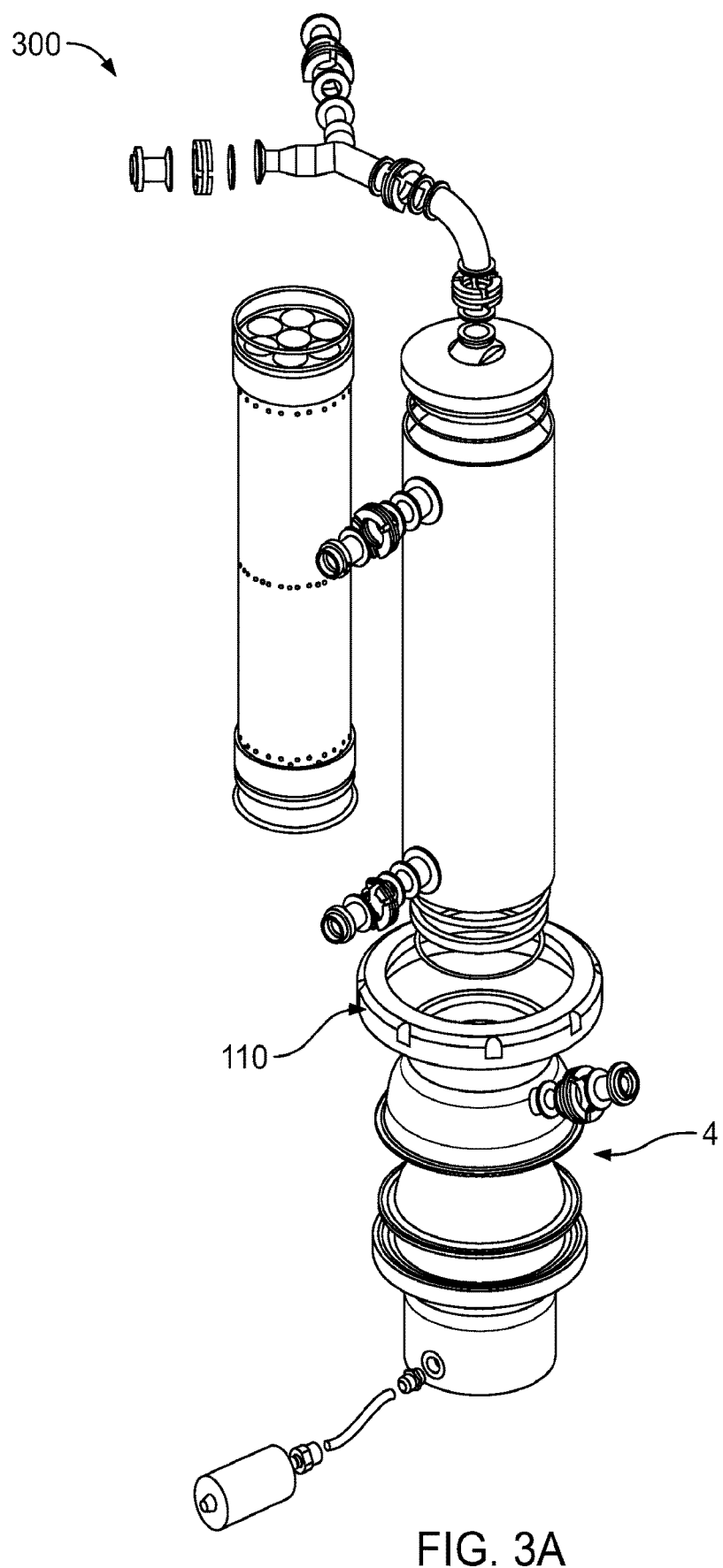
FIGS. 3A-3C are isometric, front, and cross-section views of a third embodiment of a disposable ATF housing and pump unit as described herein.
Figure 3B:
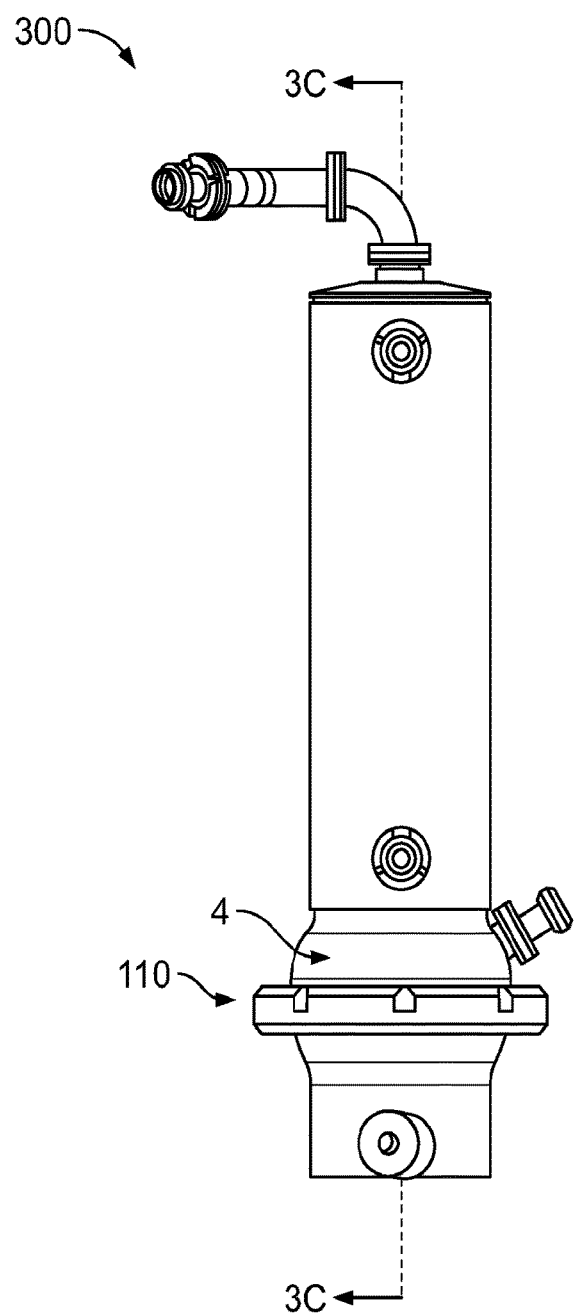
Figure 3C:
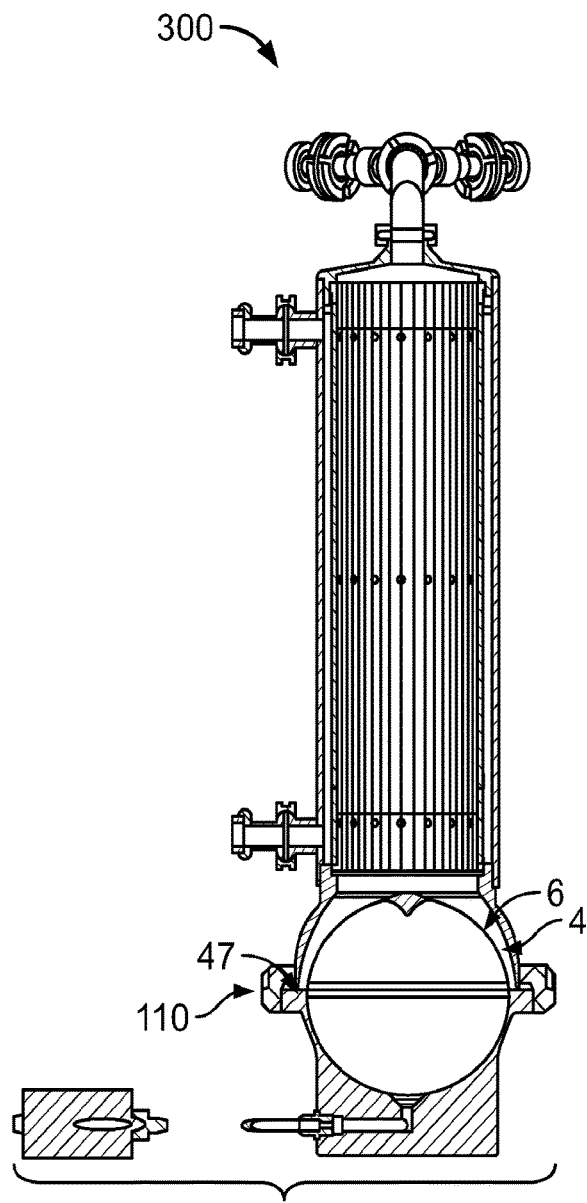

FIGS. 2A-2C are views of a second embodiment of a disposable ATF housing and pump unit 200 that also includes the disposable clamp ring 110, and FIGS. 3A-3C are views of a third embodiment of a filter assembly 300 that also includes the clamp ring 110. As shown, the disposable clamp ring 110 of this disclosure can be used with a variety of filter assembly arrangements. Dimensions shown in the figures are intended to illustrate a specific example, and are not intended to be limiting.

Figure 4A:
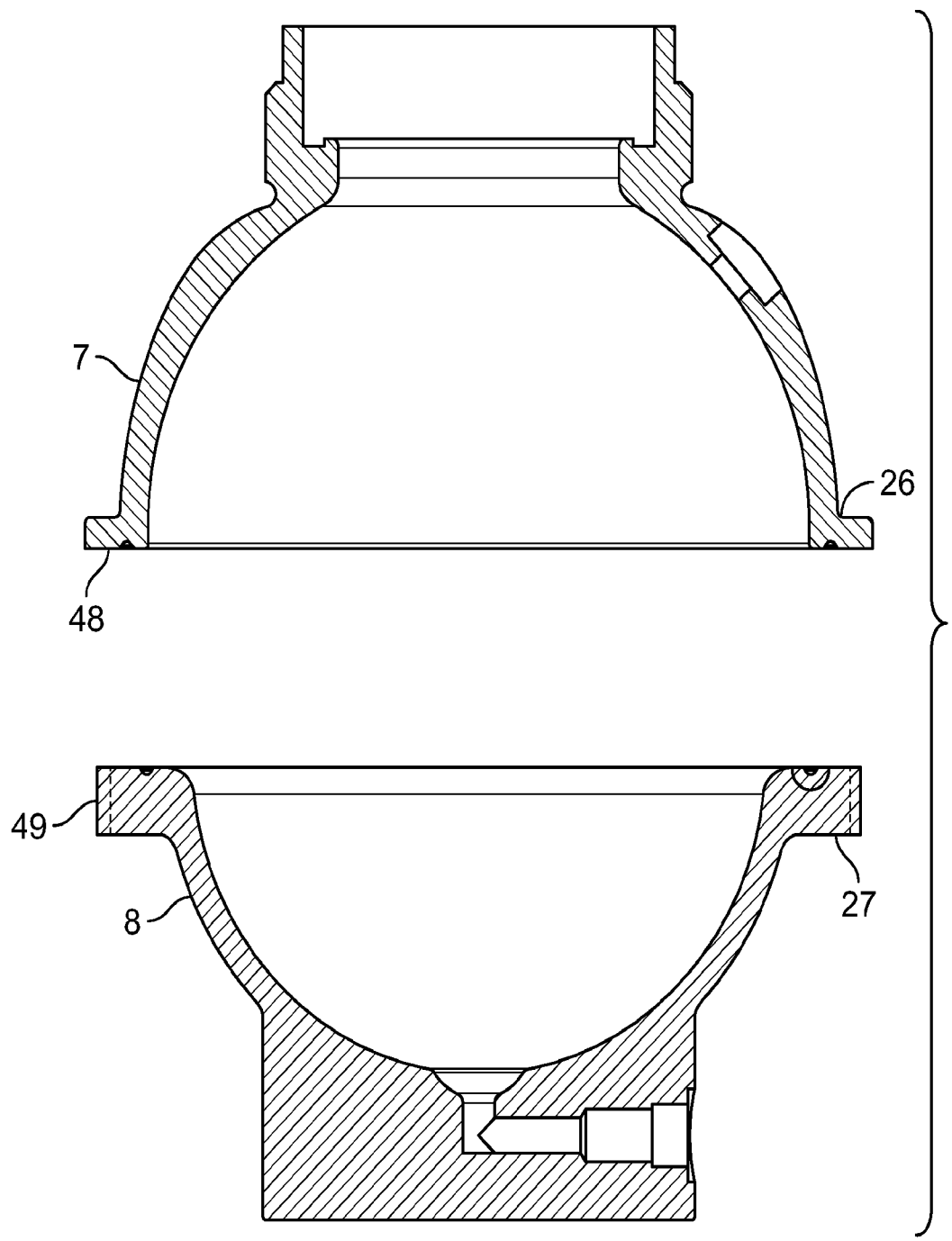
FIGS. 4A-4E are detailed views of a diaphragm pump showing the liquid side hemisphere (top), air side hemisphere (bottom), diaphragm (sealed between the hemispheres), and a lock ring, which is used to hold the hemispheres together and force compression across the diaphragm, and the sealing features added to aid in sealing pumps having larger diameters.
Figure 4B:
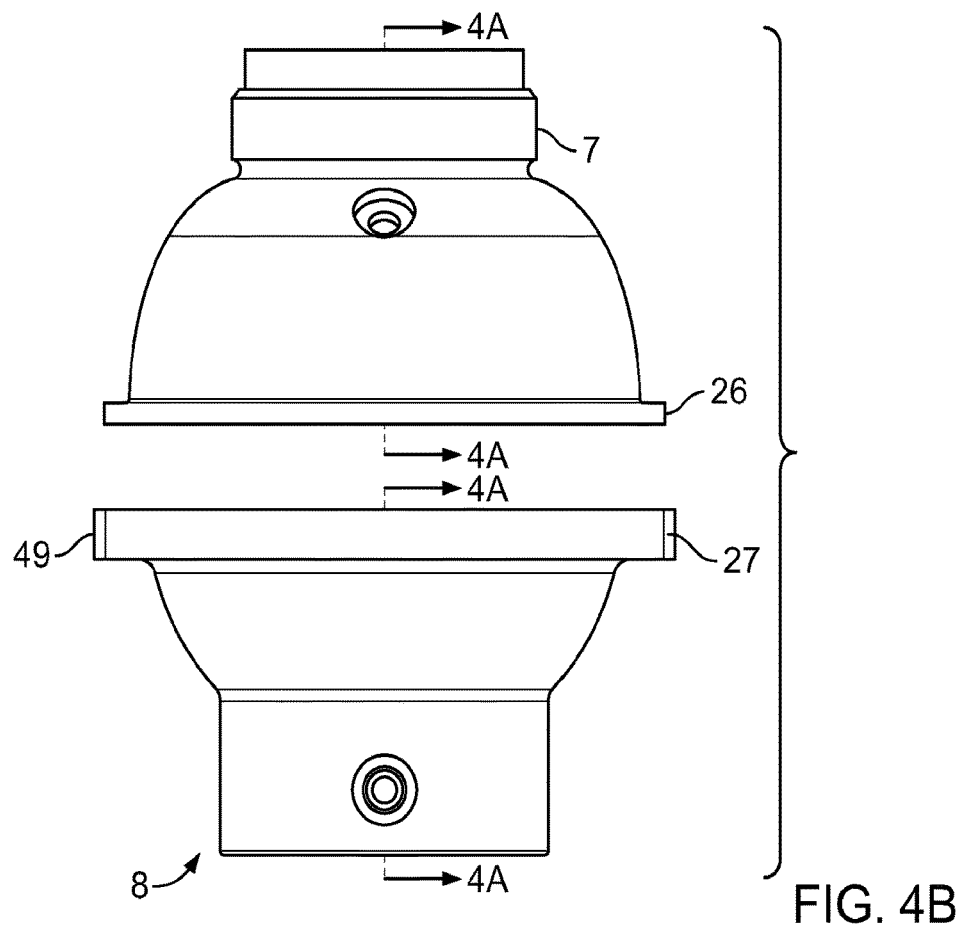
Figure 4C:
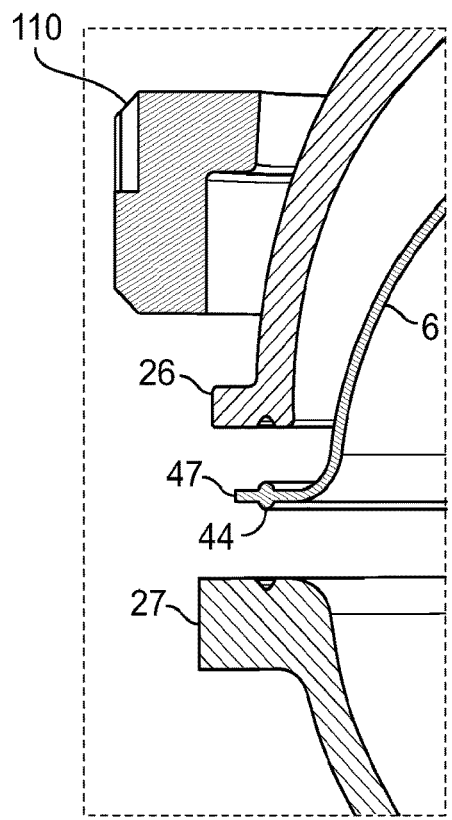
Figure 4D:
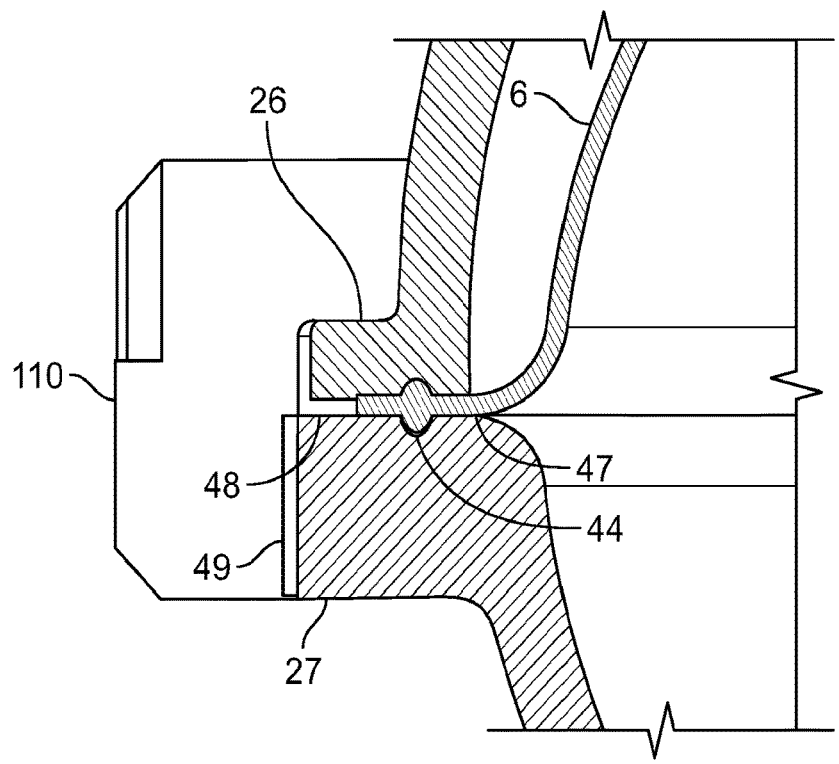
Figure 4E:
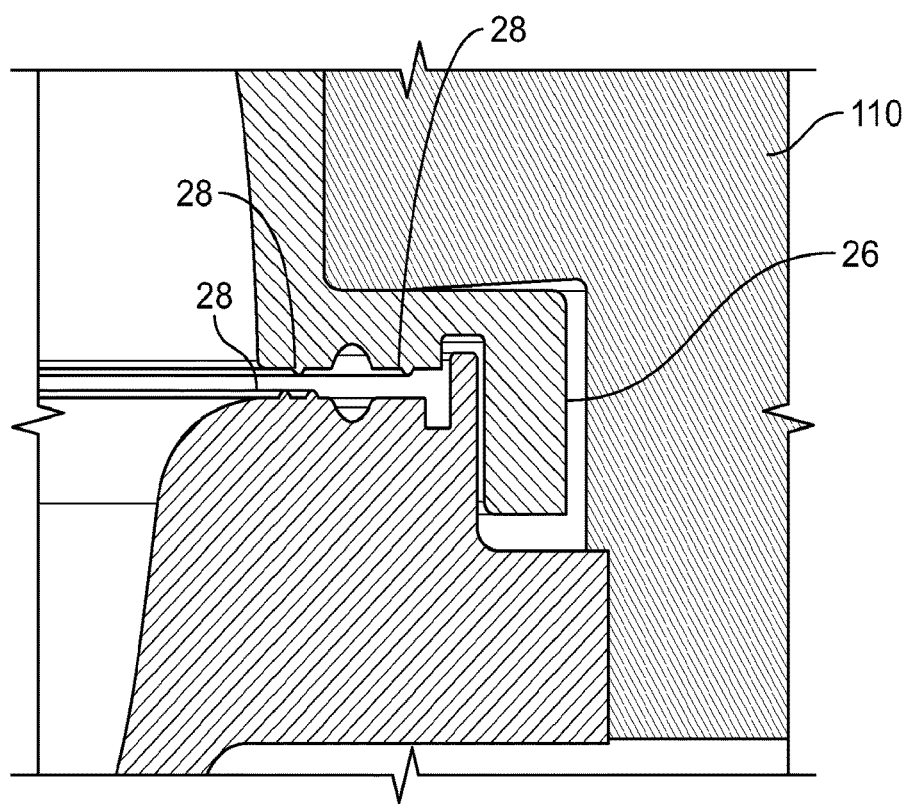

FIGS. 4A-4E illustrates the bottom, ATF pump portion of the disposable ATF housing and pump units 100, 200, 300 shown in FIGS. 1C, 2C, and 2C, and which include the diaphragm pump 4 with disposable clamp ring 110, which is used to fix a diaphragm outer flange 47 of the flexible internal pump diaphragm 6, between liquid receiving chamber 7, and air side chamber 8 with a leak-proof connection. The top and bottom hemispheres of the ATF pump each include a flange 26 and 27, respectively between which the ATF pump diaphragm 6 is sandwiched when the two hemispheres are assembled. Flange 27 of the lower half of the ATF pump comprises an external threading to be used to engage the disposable clamp ring and compress both flanges across the diaphragm. FIG. 4E shows the details of features added to aid in sealing across the diaphragm in larger diameter pump geometries.

Figure 5A:
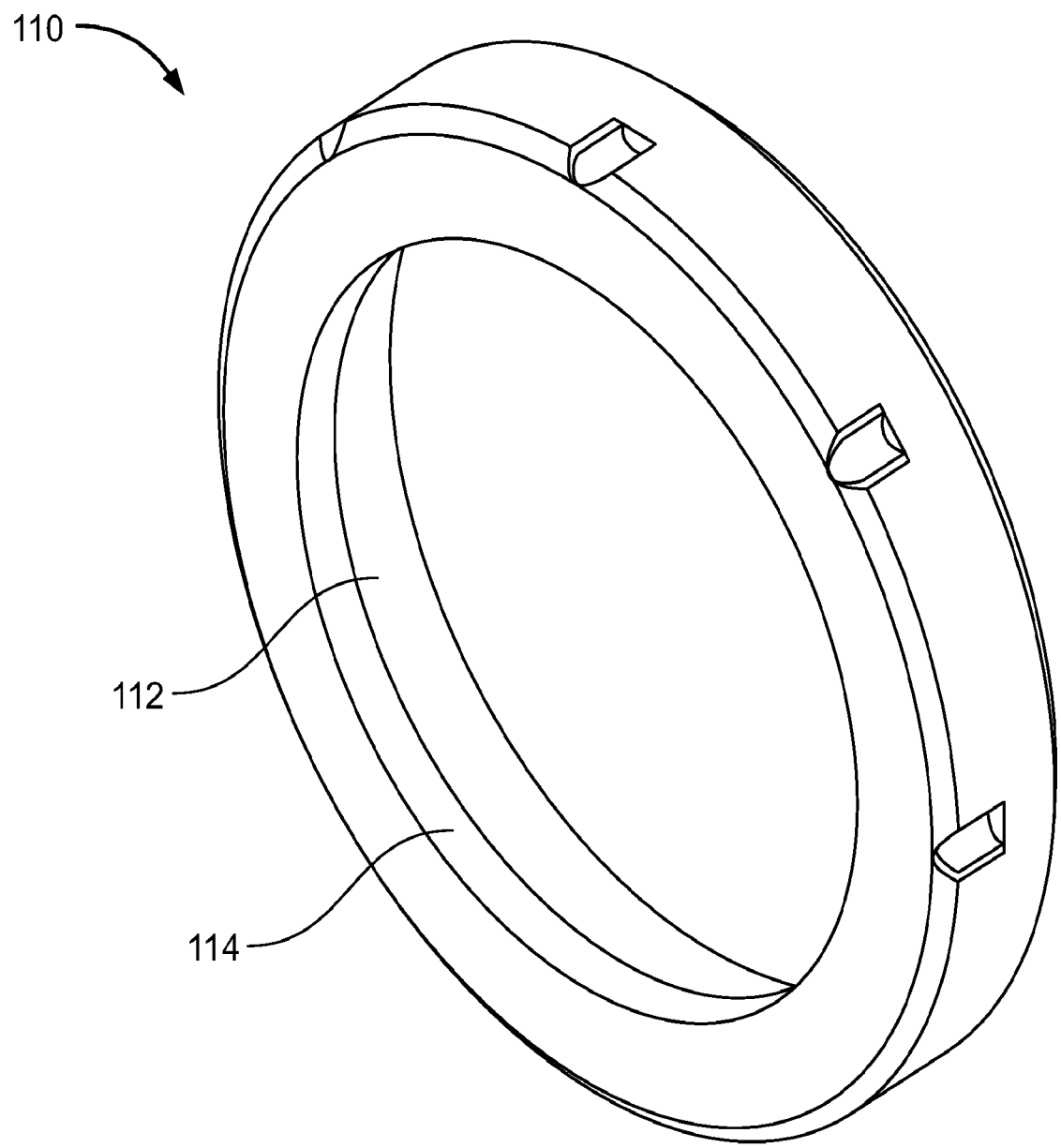
FIGS. 5A-5C are isometric, cross-sectional, and top views of an internally threaded plastic clamp ring specifically designed for use with ATF diaphragm pump assemblies having externally threaded flanges as described herein.

Referring as well to FIG. 5A, disposable clamp ring 110 is a cylindrical clamp that encloses and seals the internal diaphragm 6 between the peripheral flanges 26 and 27 of the two pump half chambers, by encircling the peripheral flanges 26 and 27 on their outer circumference, as well as a top portion of the flange 26. As noted, the outer radial contact surface 49 of at least the lower (in these embodiments) flange 27 is threaded, i.e., the radial circumference of the peripheral flange 27 has threads that contact and mate with threads on the lower inner surface 112 of the disposable clamp ring 110 at the radial contact surface 49. In some embodiments, the other flange 26 (the top flange in these embodiments) may or may not include an external thread. Other embodiments show a two piece lock ring setup with a bottom ring that threads into a top ring internally or externally to compress across the flanges.

The peripheral flanges 26 and 27 work together with the disposable clamp ring to secure the diaphragm outer flange 47 between the upper and lower surfaces of flanges 26 and 27, respectively. In some embodiments, the diaphragm pump peripheral flanges 26 and 27 are spaced from each other by a distance somewhat less than the corresponding thickness of internal diaphragm outer flange 47 such that when the two facing peripheral flanges 26 and 27 are forced together by screwing on disposable clamp ring 110, they compress to squeeze diaphragm outer flange 47 between the two peripheral flanges 26 and 27. In this design, 10-30% compression across the diaphragm is sufficient to seal both the air and liquid sides of the hemisphere.

Different levels of compression are needed for different ATF system sizes, with the larger ATF sizes requiring higher compression to contain their diaphragms and create a robust seal. Alternatively, additional features can be added to increase and/or decouple sealing and containing the diaphragm at high pressures (FIG. 4E). Examples of these features are energy director protrusions 28 which are additional protrusions and/or grooves worked into one or both inner flanges to provide additional compression and/or sealing across the diaphragm. As shown particularly in FIGS. 4C-4D, flanges 26 and 27 can contain a groove that is designed to accept a counterpart O-ring 44 portion or protrusion of the internal diaphragm 6. Once in contact, the periphery of peripheral flanges 26 and 27 can be sealed to each other along their contact surfaces of their opposing faces. In the process, internal diaphragm 6 is sealed securely between the two peripheral flanges 26 and 27.

The new methods allow for setting the magnitude of the compression on internal diaphragm outer flange 47 by controlling the compression distance between corresponding and adjacent pump flange segments. Alternatively, a torque specification can be measured that correlates to sufficient compression of the diaphragm to contain pressure at several orders of safety in the design. The torque specification required to seal each ATF system is different. The larger the ATF system the larger the torque needed on the lock ring to compress the diaphragm. For example the ATF2 system 100 series, only requires 10-20 lbft while the ATF10 300 series requires 80+ lbft. An ATF system sized between these two examples would require between 20-90 lbft.

Figure 5B:
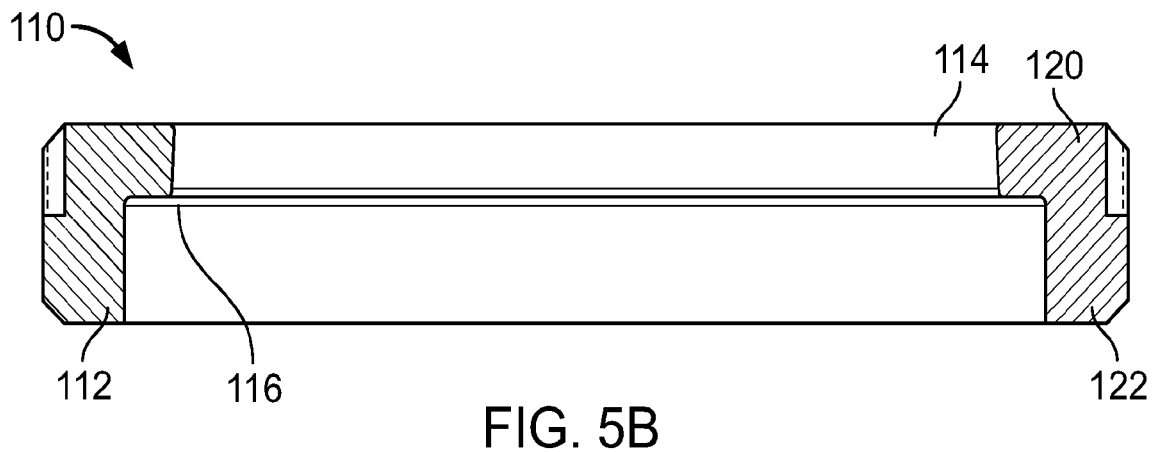
Figure 5C:
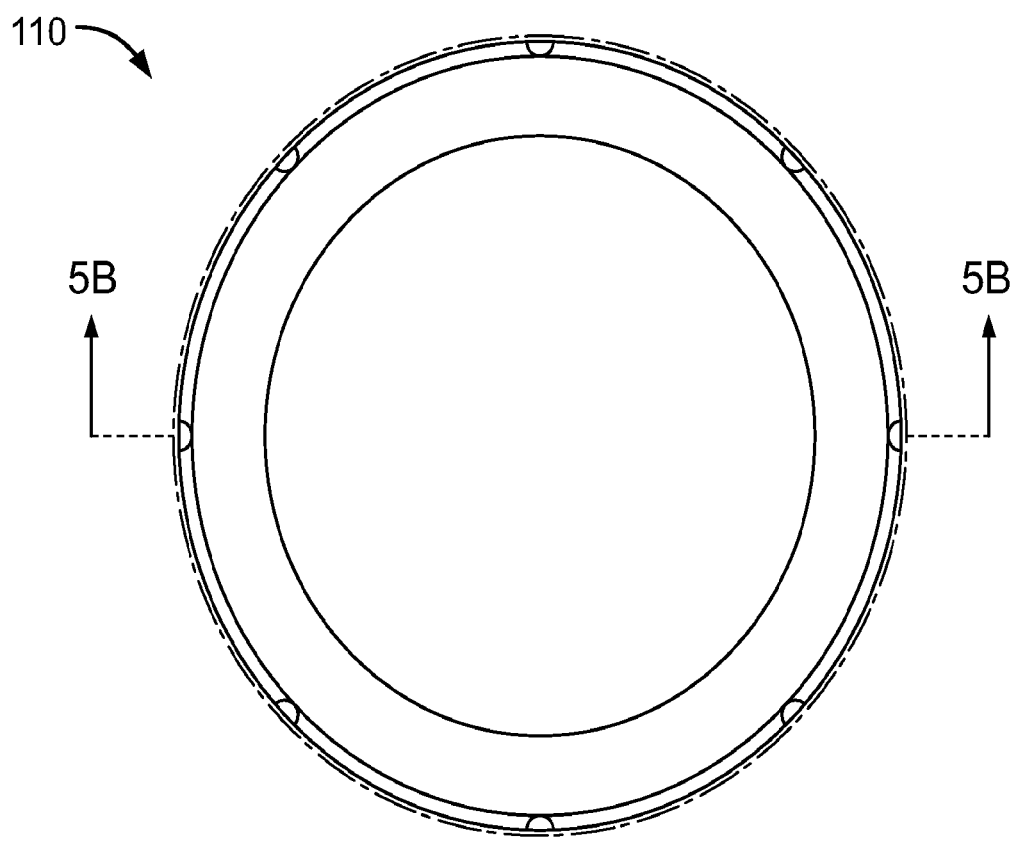

Referring as well to FIGS. 5A-5C, disposable clamp ring 110 has an upper portion 120 and lower portion 122. The upper portion 120 has a smaller inner radius compared to the lower portion 122. The inner (e.g., radially closest to the centerline) surface of the lower portion 122 is referred to herein as lower inner surface 112, which is threaded and which engages with the radial perimeter outer surface of peripheral flange 27 of the ATF pump drive chamber 8. The inner surface of the upper portion 120 is upper inner surface 114, which is radially closer to the centerline compared to the lower inner surface 112.

The upper inner surface 114 engages with an outer surface of the liquid receiving chamber 7. As shown in the figures, the liquid receiving chamber 7 is a hemisphere and thus has a curvature, rather than being a flat surface. To accommodate, and to sealingly engage with the external surface of the liquid receiving chamber 7, the upper inner surface 114 is angled at an angle α to the horizontal. The angle α can be 0-5°, e.g., 1.0, 1.5, 2.0, 2.5, 3.0, 3.5, 4.0, or 4.5°, but is adjusted as required to accommodate the curvature of variously sized hemispheres of differently-sized ATF diaphragm pumps 4. This mating surface reinforces the upper hemisphere during high pressure conditions. The upper and lower hemispheres do not touch during assembly, they are forced together, but are separated by the compressed diaphragm.

Systems and Processes for Use with Disposable ATF Pumps

In general, the new disposable ATF pumps can be used with enclosed filtration systems that employ a retentate chamber and a filtrate chamber, e.g., as shown in FIG. 6A and described in further detail below. Such ATF filtration systems and ATF pumps have been described in Shevitz, U.S. Pat. No. 6,544,424.

A convenient way to create a retentate chamber and filtrate chamber in the new disposable ATF pumps is to use a hollow fiber filter cartridge. Such a filter is made as a cartridge that comprises multiple hollow fibers (HF) that run in parallel along the length of the cartridge and are embedded at each end of the cartridge (preferably with a potting agent); the lumens at the end of the HFs are retained open, thus forming a continuous passage through each of the lumens from one end of the cartridge to the other, i.e., from a cartridge entrance end, to a cartridge exit end. The hollow fibers are enclosed by the outer wall of the cartridge (i.e., the cartridge wall) and a potting layer at their ends. As a result, there is a chamber bounded by the cartridge wall and the outer walls of the HFs. That chamber can be used as the filtrate chamber. The intra-luminar (internal) spaces of the HFs are considered collectively to constitute part of the retentate chamber in each of the present systems.

Figure 6B:
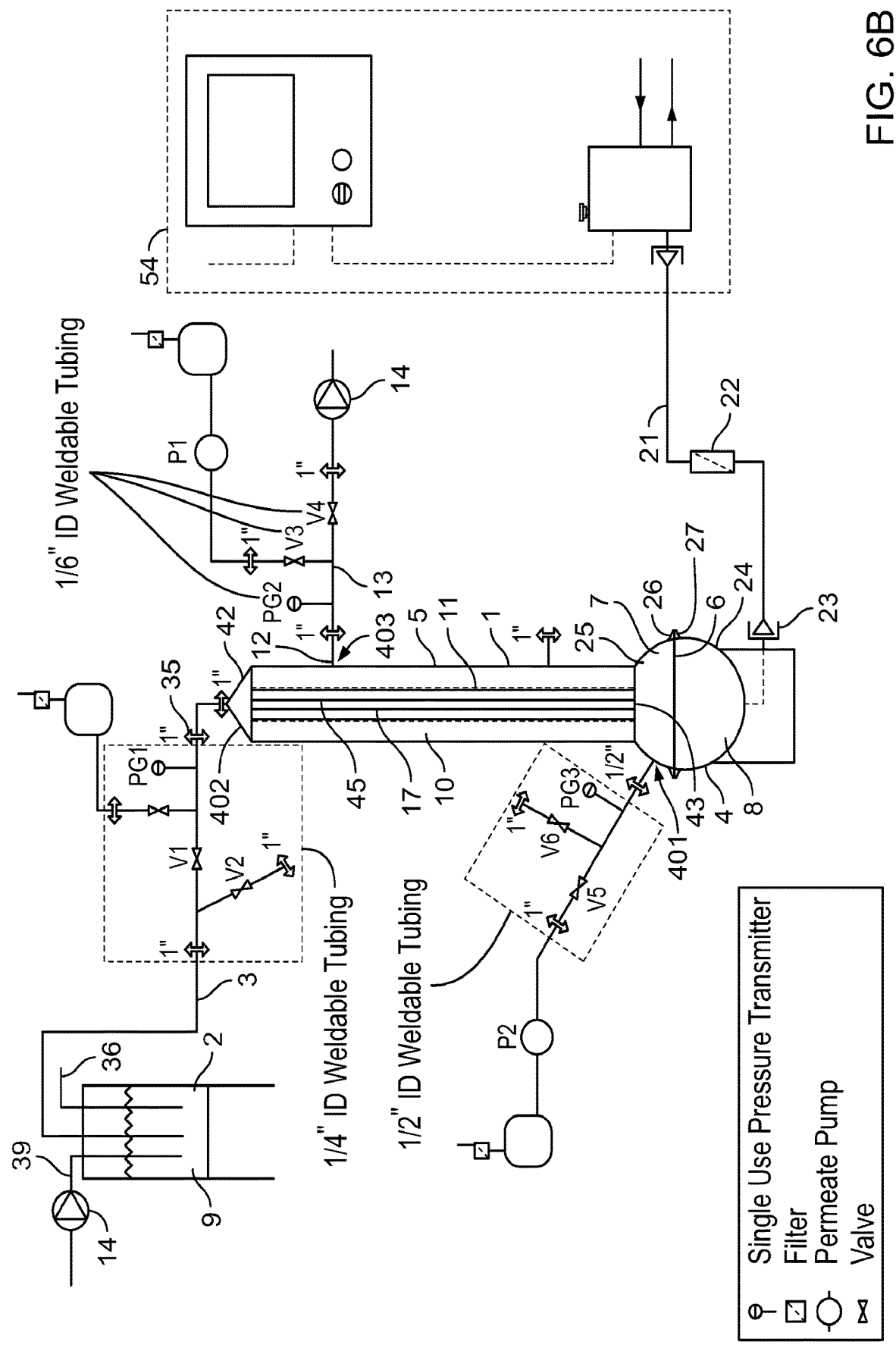
FIG. 6B is a system level representation of the disposable ATF pump housing connected to a controller and a bioreactor and fluid bags and ports used to flush and condition the filter prior to cell culture production.

The retentate chamber is extended beyond the internal spaces of the HFs by adapters that fit to each end of the cartridge. Each adapter in conjunction with an end of the cartridge defines a space that is part of the retentate chamber. Depending on the direction of fluid flow through the fibers, that space serves to either (1) collect fluid as it exits the fibers or (2) allow fluid arriving from an external source to interface with the HF open ends and distribute itself among those HFs for purposes of continuing its path towards the other end of the cartridge. Each adapter will have two ends, one end fitted to the cartridge and the other end with an opening connectable to a vessel or a pump. Normally as is shown in FIG. 6A-6B, the vessel is connected to the adapter by a line that allows fluid flow but, if desired, the vessel can be connected directly to the adapter or the adapter may form part of the vessel where part or the entire content of the vessel may be contained within the adapter. Normally the adapter is connected directly to the disposable ATF pump but, if desired, the pump can be connected to the pump via a line that permits fluid flow.

When a connecting line is added to an adapter, the retentate chamber is extended to also include the space inside that connecting line. When a connecting line is connected at one end to an adapter and at its other end to a vessel (e.g., one that contains cells suspended in growth medium), one could consider the interior of the vessel to be a further extension of the retentate chamber, but for purposes of description and discussion herein the vessel and the retentate chamber are referred to as separate entities.

The walls of the lumens of a hollow fiber filter are permeable, conveniently providing a barrier that is either fully permeable or selectively permeable. The selectively permeable hollow fiber walls may range in selectivity that ranges the entire gamut of membrane pore sizes, commonly classified as osmotic membranes, and from ultrafiltration microfiltration to macrofiltration and also micro-carrier filtration, where, for example,), the pore size range is about 10-500 kDa and 0.2-100 micron. Pore sizes of about 0.2 micron are commonly used for retaining cells and allowing metabolites and other molecules or molecular complexes to pass throughout the pores. On the other hand, ultrafiltration pore sizes in the range 10 kDa to 500 kDa, are preferred for retaining not only the cells, but molecules and molecular complexes, e.g., produced by the cells, that are larger than the pore sizes. Macrofiltration membranes range from 7 to 100 um and are used to retain microcarriers or larger cells. These selectively permeable hollow fibers must be wet with a liquid compatible with the fluid substance be filtered. For example in cell culture the membrane must be wet with water based solutions that are compatible with cell culture growth. Many membranes require alcohol containing solutions to initially wet the pores and achieve flux rates during operation that are needed to perform the filtration process. FIG. 6B shows the ports and fluid bags that can be used to add fluid to the ATF device. Flushing with serum free media in a sterile environment can then be performed using the alternating pumping action of the ATF device. Then the flush fluid can be drained from the port and the device is ready to operate in the cell culture process while maintaining a sterile environment.

The outer walls of filter cartridges, e.g., for use in the new disposable ATF housing and pump units, are often non-permeable and commonly have ports from which filtrate can be drained and/or replaced. For purposes of some embodiments of the enclosed filtration systems, however, the filter cartridge can include an outer wall that constitutes a barrier that may be non-selective (fully permeable), but is preferably semi-permeable, (not allowing dissolved matter (e.g., molecules and molecular complexes) larger than the pore sizes in the barrier to pass through the barrier and not allowing particulate matter larger than the pore sizes to pass through the barrier). Pore sizes in the range 10 kDa to 500 kDa are preferred for retaining only molecules and molecular complexes larger than the pore sizes. However, the pore sizes can be made small enough or large enough, so that, respectively, the barrier is highly restrictive, allowing only small salts and their components to pass through or allowing molecules or particles larger than 500 kDa to pass through the membrane. Such membrane selectivity is not only restricted to pore size but to other membrane properties, including: charge, hydrophobicity, membrane configuration, membrane surface, pore polarity, etc.

In the typical enclosed filter preparation process, the steps generally include:

(1) discharging fluid from a retentate chamber via a fluid connector into a vessel (such as a storage vessel) such that during said discharging a portion of said fluid is directed via a semipermeable barrier into a filtrate chamber and is then directed via a selective barrier into a reactor chamber, wherein said discharging is due to the force exerted by a diaphragm pump connected to the retentate chamber at a position distal to the fluid connector;

(2) reversing the direction of the force exerted by the diaphragm pump so that at least some fluid from the vessel flows back into the retentate chamber and at least some fluid from the retentate chamber flows into the filtrate chamber (and preferably some fluid from the filtrate chamber flows into the reactor chamber); and (3) repeating steps (1) and (2) at least once, wherein fluid discharged from the retentate chamber is optimally a solution capable of wetting the membrane pores such as serum free culture media, and wherein the retentate chamber, filtrate chamber, reactor chamber, and diaphragm pump are part of the same enclosed filtration system (preferably wherein the enclosed filtration system is described in the general aspect or second aspect herein above).

In the foregoing and following process descriptions, the fact that fluid crosses a portion of a barrier in one direction does not preclude, and indeed is often associated with, fluid flow in the opposite direction at another portion of the barrier. Through this action the membrane pores are fully wetted and the designated flux rate of the filter is obtained. Once the membrane has been wetted by the ATF action the fluid can be discarded from the pump port and the device is ready to perform ATF when attached to the bioreactor.

In a variation of the enclosed filtration system process, applicable to a system that comprises a filtrate reservoir, the process includes the steps of:

(1) discharging fluid from a retentate chamber via a fluid connector into a vessel such that during said discharging, a portion of said fluid is directed via a selectively permeable barrier from the retentate chamber into a filtrate chamber, such that a portion of said fluid directed into the filtrate chamber is directed via an opening in the filtrate chamber wall to a filtrate reservoir and such that a portion of said fluid directed into the filtrate chamber is directed via a selective barrier into a reactor chamber, wherein said discharging is due to the force exerted by a diaphragm pump connected to the retentate chamber at a position distal to the fluid connector; and (2) reversing the direction of the force exerted by the diaphragm pump so that at least some fluid from the vessel flows back into the retentate chamber, at least some fluid from the retentate chamber flows into the filtrate chamber, at least some fluid from the filtrate chamber flows into the filtrate reservoir.

(3) repeating steps (1) and (2) at least once, wherein fluid discharged from the retentate chamber is selected from the group consisting of a suspension and solution, and wherein the retentate chamber, filtrate chamber, reactor chambers and diaphragm pump are part of the same filtrate reservoir system, (preferably wherein the filtrate reservoir system is described herein above).

FIG. 6A shows an enclosed fluid filtration system 1 connected via a fluid connector 3 to a process or cell culture vessel 2 that contains the fluid material or retentate 9 to be processed. The fluid filtration system 1 contains at least two chambers: a retentate chamber 45 confining the unfiltered material on the inside of the fiber lumens and a filtrate chamber 10 within the filter housing 5.

The fluid filtration system 1 is the new disposable ATF housing and pump units. In general these units are enclosed by filter housing 5, whose shape, size or orientation may be varied as needed to enclose the system. The filter housing 5 may be constructed from a variety of materials, including solid polymers, such as polycarbonate or polysulfone, flexible or elastic materials, glass-filled polymers, or any other materials or composites of materials that meet the requirements of strength, non-toxicity, and sterilizability as described herein. The fluid filtration system is connected to a process or cell culturing vessel 2 via a fluid connector conduit 3.

The process vessel 2 may be any suitable container for a fluid to be processed. For example, it may be a bioreactor, a circulatory system (e.g., for a human or animal patient or subject) or any other vessel, nonexclusively including tanks, bags, flasks and the like, which can contain liquids. The process vessel 2 may be composed of any suitable material or combination of materials, including, synthetic polymers, inert metals, such as stainless steel, glass, etc.; nor shall they exclude rigid, flexible or elastic materials or a combination thereof; nor should such materials be limited in shape, size or configuration, as long as they result in a process vessel. The process vessel 2 is not limited as to accessibility: it may be modified to allow additions to or subtractions from the content of the vessel. Lines or tubes 36 and 39, for example, can be used to effect additions to or subtractions from the content of process vessel 2, for example using a pump 14 to control such addition or subtractions. Such process vessels are commercially available in all sizes and configurations, and are well known to those in the field.

The fluid connector 3 serves to direct a fluid from the process vessel 2 via fluid exchange port 35 to the entrance end 42 of filter element 11 which also corresponds to the entrance end of the retentate chamber 45. Entrance end 42 while serving as an entrance to retentate chamber 45, may also serve as a reservoir for retentate; its shape and positioning may be varied according to need; its volume may be approximately equal to or less than the diaphragm pump displacement volume, facilitating between entrance end 42 (reservoir) and pump, and further facilitating greater level of retentate concentration and recovery of final concentrate.

The fluid flow is further directed through the filter channels 17, which would correspond to the interiors of the lumen(s) of a hollow fiber filter should filter element 11 correspond to a hollow fiber filter. The filter channels collectively correspond to the retentate chamber 45 of the fluid filtration system L In one direction, the fluid flow proceeds to, and exits from, the exit end 43 of the filter element 11. The exit end 43 of both the filter element 11 and the retentate chamber 45 connects directly to a liquid receiving chamber 7 of a diaphragm pump 4. Alternatively, the filter exit end 43 may be connected to the diaphragm pump 4 through a conduit (not shown here).

The ATF diaphragm pump 4 as described herein generates the flow through the filter element 11 between process vessel 2 and back to the pump. As described above, the ATF diaphragm pump 4 preferably comprises a pump housing separated into a drive chamber 8 (the first interior chamber) and the liquid receiving chamber 7 (the second interior chamber), by an internal diaphragm 6. The pump housing is made of two housing components, the first pump housing component 25 and the second pump housing component 24. The components comprise peripheral flanges 26 and 27, respectively. Pressure in the drive chamber 8 drives the diaphragm within diaphragm pump 4 without causing contamination of the fluid content in the liquid receiving chamber 7.

For example, the pump can be an air driven pump. Compressed air is directed by controller 54 to drive chamber 8 through line (tube) 21, preferably through a sterilizing filter 22 and an air inlet port 23. Increasing the air pressure in drive chamber 8 relative to process vessel 2 drives a flexible internal diaphragm 6 into liquid receiving chamber 7, driving liquid in that chamber through the filter element 11 to vessel 2. The reverse flow from process vessel 2 to diaphragm pump 4 is generated by reducing the pressure in drive chamber 8 relative to the vessel 2. The cycles are repeated. Alternating flow generated by such a pump has been described in U.S. Pat. No. 6,544,424.

The filter element 11 is a made as a cartridge that comprises multiple hollow fibers (HF) that run, in parallel, the length of the cartridge, from a cartridge entrance end to a cartridge exit end. A segment of the hollow fibers are externally potted at both ends of the cartridge, by methods common to manufacturers of hollow fiber cartridges; the hollow fibers are enclosed by a perforated wall 19 which is then sealed to an outer housing via O-rings or other means. Examples of potting compounds are epoxies and polyurethanes. As a result, there is a chamber bounded by the perforated cartridge wall 19 potted ends and the filter channels 17 of the HF. That chamber is a segment of the filtrate chamber for the present invention. However, for purposes of description, the intra-luminar spaces are considered collectively to constitute a retentate chamber in each of the present systems. Alternatively the fiber membranes can be potted directly into the outer filter housing 5.

The harvest from system 1 is collected via line 13 which is connected to harvest port 12, which allows fluid flow from the filter housing 5 and that line so as to allow fluid to leave the system 1 via pump 14.

The filter channels 17 corresponding to the walls of the lumens (hollow fibers) of the illustrated hollow fiber filter are selectively-permeable, conveniently providing the selectively permeable wall referred to in the descriptions of the systems. The outer wall 19 of the filter cartridge (the cartridge wall) is perforated to allow fluid flow to harvest port 12.

EXAMPLES

The invention is further described in the following examples, which do not limit the scope of the invention described in the claims.

A variety of testing and experimental procedures were required to produce a disposable clamp that can withstand the pressures inside a diaphragm pump 6 of fluid filtration system 1.

Example 1

Pump Hemisphere Pressure Test

Figure 7:
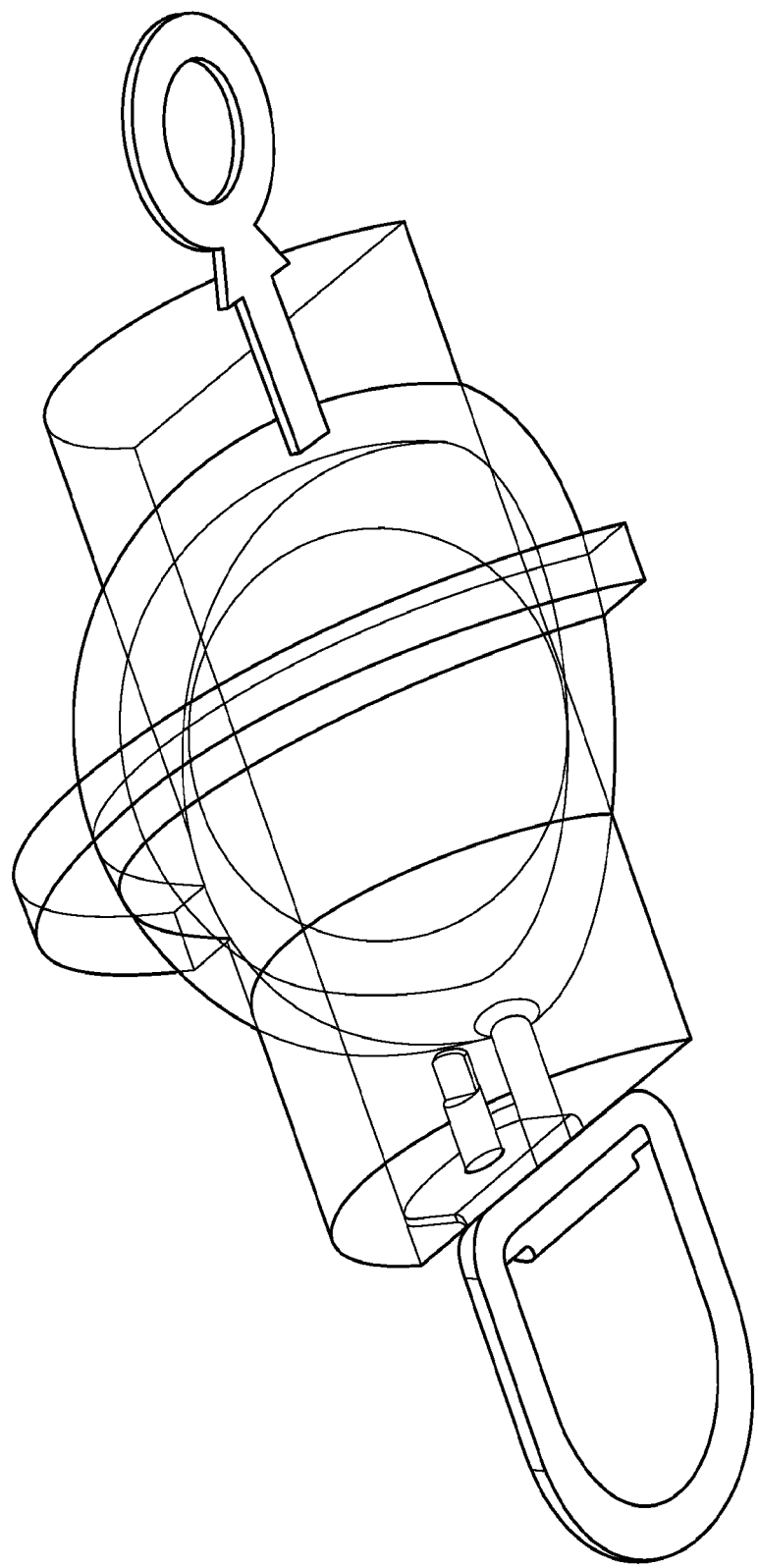
FIG. 7 is a representation of a pump hemisphere test apparatus used in testing described in the examples described herein.

The pump hemisphere test apparatus 55 design is shown in FIG. 7. The design differed from a stainless steel standard pump in regards to the methods used to hold the silicone pump diaphragm in compression. A flat flange outside of the silicone diaphragm on either half of the pump was added so that these could be secured together using various methods of attachment, and a small "shelf" feature was included on one pump half to prevent over-compression. The assembly also had holes to allow the attachment of a large steel eye-hook and a steel tie-down hook to enable failure testing with an Instron® machine (for strength analysis of the different attachment methods).

After assembling the pump hemispheres with different attachment methods such as solvent welding, UV cure adhesive, and mechanical fastening using screws, clamping, or a circular ring clamp as described herein, we pressurized the air side hemisphere until the diaphragm seal leaked. To properly compress the diaphragm and get a good glue adhesion, we needed to localize the force from the OPUS packing stand linear actuator. This was achieved using a large diameter acrylic tube for the top and bottom halves of the pump. We glued two pumps using multiple vice clamps to provide the localized force at the outer edge. In addition we used eight evenly-spaced ¼-20 polycarbonate screws on the outside portion of the pump for one unit while UV gluing it, and for another unit we used 16 of these screws in addition to UV gluing. These units were subjected to 5 PSI increases every few minutes, stepping up to the point of failure.

The pump hemisphere pressure test revealed to us that we are dealing with forces significantly larger than we initially expected. For example, the ATF10 system running at 45 PSI, must withstand up to 13,500 lbf. The hemisphere that was glued with UV cure adhesive and bolted together with 16 polycarbonate fasteners failed extremely violently at 45 PSI. It jumped 3 feet into the air and actually bent a stainless steel bolt that was used in the place of one stripped polycarbonate screw. The burst pressure results are described in Table 1 below.

TABLE 1

Pump Hemisphere Pressure Test Results

| Assembly Number | Assembly Description | Burst Pressure |
| --- | --- | --- |
| 1st | 7650 lb force under linear actuator with force directing acrylic tubes with 5% doped methylene chloride | 25 PSI |
| 2nd | 7900 lb force under linear actuator with force directing acrylic tubes with 5% doped methylene chloride | 10 PSI |
| 3rd | 8 vice grip clamps with 5% doped methylene chloride | 5 PSI |
| 4th | UV cure adhesive with 8 polycarbonate screws | 20 PSI |
| 5th | UV cure adhesive with 16 polycarbonate screws | 45 PSI |
| 6th | Clamp Ring | 55 PSI |

Thus, of all of these different attachment methods to secure the top and bottom hemispherical pump chambers together, only the clamp ring system as described herein succeeded in holding a leak-proof seal up to 55 PSI. While the clamp ring held the most pressure, we could have applied even more torque, and thus provide even greater pressure resistance, so we have developed a specific wrench design to gain maximum leverage

Example 2

Preparation of a Disposable ATF Device Using Serum Free Media as a Flushing Solution and Operation of the ATF Device to Attain Membrane Wetting With reference to FIG. 6B, the following is a procedure designed to flush a hollow fiber membrane quickly and efficiently using ATF technology. This flushing benefits the user by wetting, conditioning, lowering endotoxin, and removing total organic compounds (TOC) from the membrane with one method. Using the ATF is advantageous over other methods as it requires less volume and can be performed with ease within a closed sterile system without using solutions not compatible with cell culture growth. ATF run rates for various size disposable ATF devices is provided.

Procedure
1. Connect "T" tubing sets to feed 401, retentate 402 and upper permeate 403 ports. The upper permeate port can be the upper port 102 as shown in e.g., FIG. 1.
2. Attach reservoir with wetting agent to "T" off of port 401.
3. Attach container to "T" off of port 402.
4. Attach a collection bag off of "T" at port 402.
5. Fill ATF from port 401 with a pump until bag off of port 402 sees wetting agent
6. Begin running ATF at rate shown in Table 1.

| suATF Size | ATF Rate Range | Recommended Rate |
| --- | --- | --- |
| 2 | 0.5-1.5 LPM (liters per minute) | 0.9 LPM |
| 6 | 8-20 LPM | 17.2 LPM |
| 10 | 40-100 LPM | 80 LPM |

7. Flush for 1 hour by harvesting from port 403 and feeding from port 401 at 5.7 liters per meter squared per hour (LMH).

8. Retentate fluid can be left in device if same as bioreactor media or can be drained from port 401 and refilled with media from the bioreactor prior to cell culture production operation.

Example 3

Using a Conditioned ATF Disposable Device for Filter Integrity Testing

Also referring to FIG. 6B, a filter integrity test is a means to insure that the hollow fiber membranes are intact and the membrane pores are fully wetted. After flushing in ATF mode, drain the wetting fluid (media) back into the wetting fluid bag via gravity or by reversing Pump P2 with air source open to 1-2 psi to raise the diaphragm and all other valves open. The bag should be positioned to allow draining.

After draining, close the air source valve and release any pressure on the diaphragm. Then close the valve located between the wetting agent bag and port 401 and the valve along the line connected to retentate port 402, and remove tubing from pump P1. Slowly pressurize the feed side of the filter using air pressure source. Close valve between the filter and the air pressure source and time the pressure decay versus time. Correlate this to air flow. Valve at connected to the collection bag via port 403 is open during the decay test. Optionally a flow meter could be added that line and in that case the pressure source would remain open and the air flow integrity would be measured.

Disconnect the flush/integrity bag set-up after this by using tubing welder or valves/clamps or other means in order to maintain sterility.

Example 4

Operating an SU-ATF with a C410 Controller for Diaphragm Lifetime Testing

A disposable ATF6 with a 0.2 µm Spectrum PES filter was connected to a Repligen C410 controller. The A2B connection was connected to a water bath at 40° C. and ran for 500,000 Pressure and 500,000 Exhaust cycles at an ATF Rate of 17.2 liters per minute (LPM). Permeate was pulled at 5.7 LMH as it would be used in a perfusion process to keep the operation as similar to a bioreactor condition as possible. This leads to approximately 10,000 Pressure and 10,000 Exhaust cycles per day. The ATF ran for 50 days while monitoring diaphragm displacement volume. The displacement volume remained constant throughout the entirety of the 50 day run maintaining a constant flow rate as expected.

Example 5

Production of Monoclonal Antibodies in a CHO Perfusion Bioreactor with SU-ATF2

Figure 8:
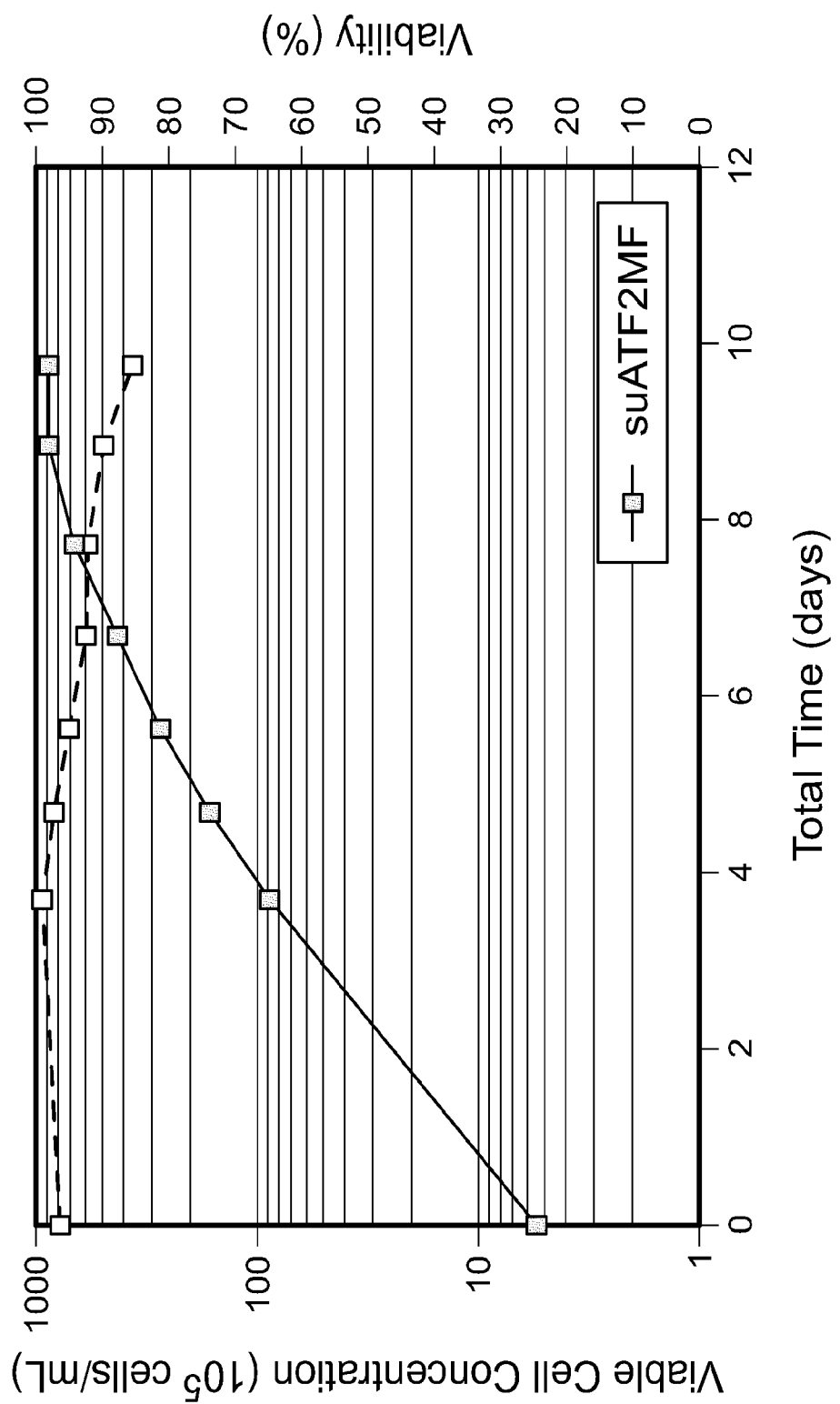
FIGS. 8 and 9 are graphical results of cell cultures performed using the ATF pump housing of this disclosure.
Figure 9:
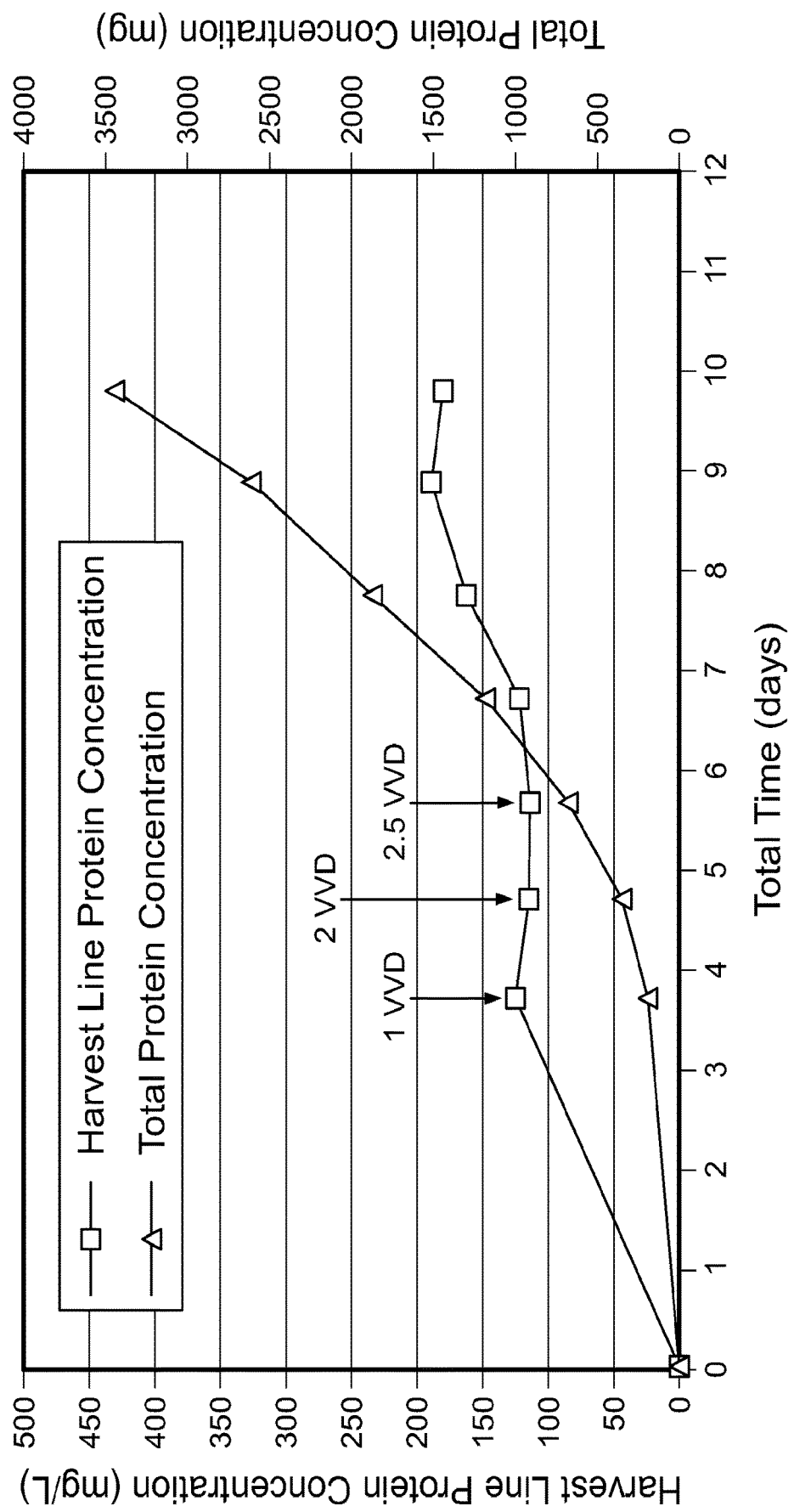

Cells cultured using the ATF filters of this disclosure were tested, and results are shown in FIGS. 8 and 9. A gamma irradiated sterile suATF2 filter (0.2 µm polyethersulfone microfilter with 0.13 m$^2$ surface area) was tested in a monoclonal antibody-producing CHO cell perfusion process. After gamma sterilization process, the suATF2 filter was connected to a 5.0 L bench scale bioreactor (at 1.5 L working volume) using sterile GE Readymate® connectors. A C24Uv2.5 ATF controller was used to operate the suATF2 filter. Prior to inoculation, the suATF2 filter was flushed with 1.5 L of CD optiCHO® growth medium (Thermo Fisher) contained in the bioreactor for 1 hour at an ATF rate of 0.9 LPM with a permeate rate of 12.4 LPM (flux 5.7 LMH) recirculating in the bioreactor. The filter was flushed with media to wet the filter and to reduce endotoxin levels below 0.25 EU/mL.

After this process, the ATF pump was stopped temporarily and the flushed media was discarded from the bioreactor and the suATF2 filter in a sterile manner.

A2B (ATF to Bioreactor) connection was clamped and 1.5 L of fresh CD optiCHO® growth media (Thermo Fisher) supplemented with 4 mM GlutaMAX® (Thermo Fisher) and 100 ng/mL LONG®R$^3$IGF-I (Repligen) were added to the bioreactor. After warming the media to 37° C., CHO DP-12 clone #1934 LR3 adapted cells (from ATCC, expressing recombinant human anti-IL-8) were inoculated at a seeding density of 5.5E5 cells/mL.

Throughout the run the bioreactor was maintained at 37° C. pH was controlled at 7.2+0.4 dead band until day 4 than controlled at 6.8±0.1 dead band using 0.1 N NaOH and $CO_2$. DO was maintained at 40% using pure oxygen either by an L-sparger or a micron sparger. Air was continuously sparged using an L-sparger for aeration and for stripping of $CO_2$. Antifoam C and glucose feed were added as needed to control foaming and to maintain glucose level above 1 g/L. The bioreactor was run on batch mode until day 4 and perfusion was initiated on day 4 at 1 volume vessels per day or VVD (1.5 L/day perfusion rate). Perfusion rate was manually increased stepwise to 2 VVD (3 L/day) on day 5 and 2.5 VVD (3.75 L/day) on day 6 until the end of perfusion run. The ATF2 perfusion bioreactor data shown below is from day 0 to day 10 (bioreactor process is still ongoing).

Resulting viable cell concentration and percent viability over days is shown in FIG. 8 (in solid and open squares, respectively). Protein concentration profile for the harvest line and total protein concentration over days is shown in FIG. 9.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A disposable alternating tangential flow (ATF) housing and diaphragm pump unit comprising:
    a hollow tube of a sterilizable, non-toxic, rigid plastic;
    a first pump hemisphere secured to an end of the hollow tube, wherein the first pump hemisphere comprises a first circumferential flange; and wherein an opening in the first pump hemisphere enables fluid to flow between the first pump hemisphere and the hollow tube;
    a second pump hemisphere comprising a second circumferential flange configured to mate with the first circumferential flange, wherein either the first circumferential flange or the second circumferential flange comprises an external threading;
    a flexible diaphragm configured to be arranged between the first and second circumferential flanges; and
    a clamp ring having an internal surface comprising an internal threading, wherein the clamp ring is configured to be placed over the pump hemisphere without a threaded circumferential flange, an upper internal surface of the clamp ring is shaped to correspond to a curved or angled outer surface of the pump hemisphere without a threaded circumferential flange, and to be secured to the threaded circumferential flange.

2. The disposable ATF unit of claim 1, wherein the clamp ring comprises one or more of acrylonitrile-butadiene-styrene, polyethylene, polyethylene, polycarbonate and polysulfone plastic.

3. The disposable ATF unit of claim 1, wherein the clamp ring comprises a lower portion comprising the internal threads and an upper portion comprising the internal surface configured to correspond to the curved or angled outer surface of the pump hemisphere without a threaded circumferential flange.

4. The disposable ATF unit of claim 1, further comprising one or more ports used to attach any one or more of an air reservoir, a permeate flush bag, and a fluid supply bag through sterile connections to achieve a closed system capable of being operated as an ATF and wet a filter membrane.

5. The disposable ATF unit of claim 1, wherein the ATF unit has a structure that can withstand a pressure of up to 450 psi without rupturing or leaking.

6. The disposable ATF unit of claim 1, wherein the first and second flanges have a groove configured to mate with a protrusion on the flexible diaphragm.

7. The disposable ATF unit of claim 1, wherein the clamp ring is configured to compress the flexible diaphragm between the first and second flanges.

8. The disposable ATF unit of claim 7, wherein the clamp ring is configured to compress the flexible diaphragm.

9. The disposable ATF unit of claim 7, wherein a level of compression can be changed by applying a torque specification that correlates to sufficient compression of the diaphragm to contain pressure at several orders of safety in the design.

10. The disposable ATF unit of claim 9, wherein the torque specification is approximately 10 to approximately 100 lbft.

11. The disposable ATF unit of claim 10, wherein the torque specification is approximately 30 to approximately 70 lbft.

12. The disposable ATF unit of claim 1, further comprising sealing features between the first and second hemispheres to aid in sealing across the diaphragm.

13. The disposable ATF unit of claim 12, wherein the sealing features comprise energy directors or raised surfaces.

14. A method of preparing a fully wetted disposable filtration device, the method comprising:
connecting retentate and permeate fluid bags to top ports of a disposable alternating tangential flow (ATF) unit of claim 1 using sterile connections;
attaching a media or other fluid containing bag to a pump inlet port; and
operating the disposable ATF unit to achieve flux of media or other fluid across a filter membrane within the hollow tube of the disposable ATF unit.

15. The method of claim 14, further comprising draining retentate fluid from the disposable ATF unit through the pump inlet port after operating the disposable ATF unit to achieve fluid flux to permeate a chamber within the hollow tube of the disposable ATF unit.

16. A method of using a disposable filtration device, the method comprising:
obtaining a disposable alternating tangential flow (ATF) unit of claim 1;
disposing the ATF unit into a fluid circuit by connecting fluid bags to top ports of the ATF unit using sterile connections, and attaching a fluid container to a pump inlet port such that the ATF unit can achieve flux of media or other fluid to be filtered across a filter membrane within the hollow tube of the disposable ATF unit; and
when the filtration is complete, disposing of the ATF unit.

17. The disposable ATF unit of claim 1, wherein the first pump hemisphere and the second pump hemisphere do not touch.

18. A method of performing an integrity test of a disposable filtration device, the method comprising:
draining media used to flush a disposable filtration device into a wetting fluid bag with an air pressure source open to raise a diaphragm inside the filtration device, wherein:
the diaphragm is arranged between respective circumferential flanges of first and second hemispheres by a clamp ring,
an opening in the first hemisphere enables fluid to How between the first hemisphere and a hollow tube of a sterilizable, non-toxic, rigid plastic secured thereto,
the respective circumferential flanges of the first and second hemispheres are configured to mate with each other,
one of the circumferential flanges comprises an external threading, and
the clamp ring is configured to fit over the hemisphere without a threaded circumferential flange and to couple with the threaded circumferential flange, an upper inner surface of the clamp ring is shaped to correspond to a curved or angled outer surface of the hemisphere without a threaded circumferential flange;
closing an air pressure source valve to release any pressure on the diaphragm;
closing a valve located between the wetting fluid bag and a port on the filtration device and a valve connected to a retentate port of the filtration device;
pressurizing one side of a filter using the air pressure source;
closing a valve between the filter and the air pressure source;
measuring the pressure decay versus time; and
correlating the measured pressure decay to air flow.

19. The method of claim 18, wherein the media is drained by gravity.

20. The method of claim 18, wherein the media is drained by pumping the media from the device.

21. The method of claim 18, wherein the air pressure source provides air at a pressure of 1-2 psi.

22. The method of claim 18, wherein the pressure decay is measured using a flow meter.

23. A disposable alternating tangential flow (ATF) housing and diaphragm pump unit comprising:
a hollow tube of a sterilizable, non-toxic, rigid plastic;
a pump chamber comprising first and second half chambers, wherein the first half chamber is secured to an end of the hollow tube, and wherein an opening in the first half chamber enables fluid flow between the first half chamber and the hollow tube;

a clamp ring; and a flexible diaphragm compressed between the first and second half chambers, wherein the first and second half chambers are secured at respective circumferential flanges by the clamp ring, wherein one of the respective circumferential flanges comprises an external threading to be secured to a threaded internal surface of the clamp rings; and an upper inner surface of the clamp ring is shaped to correspond to a curved or angled outer surface of the pump hemisphere without a threaded circumferential flange.

\* \* \* \* \*